United States Patent
Swisa et al.

(10) Patent No.: US 12,408,946 B2
(45) Date of Patent: *Sep. 9, 2025

(54) MANUAL INTRAOSSEOUS DEVICE AND METHOD FOR INTRODUCING A BONE PORTAL TO A PREDETERMINED DEPTH IN A BONE

(71) Applicant: WaisMed LTD., Rosh Haayin (IL)

(72) Inventors: Einat Swisa, Haniel (IL); Ravit Levy, Ben Shemen (IL); Naty Moskovich, Tel Aviv (IL)

(73) Assignee: SAFEGUARD MEDICAL HOLDCO, LLC, Huntersville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/651,779

(22) Filed: May 1, 2024

(65) Prior Publication Data
US 2024/0285312 A1    Aug. 29, 2024

Related U.S. Application Data

(63) Continuation of application No. 18/280,767, filed as application No. PCT/IB2022/055857 on Jun. 24, 2022.

(30) Foreign Application Priority Data

Jun. 24, 2021 (IL) .......................... 284380

(51) Int. Cl.
*A61B 17/34* (2006.01)
*A61B 10/02* (2006.01)

(52) U.S. Cl.
CPC ........ *A61B 17/3472* (2013.01); *A61B 10/025* (2013.01); *A61B 2010/0258* (2013.01);
(Continued)

(58) Field of Classification Search
CPC ............. A61B 17/3472; A61B 10/025; A61B 2010/0258; A61B 2017/3407;
(Continued)

(56) References Cited

U.S. PATENT DOCUMENTS 6,761,726 B1    7/2004  Findlay et al.
8,292,891 B2    10/2012 Browne et al.
(Continued)

FOREIGN PATENT DOCUMENTS

WO    2020261070 A1    12/2020
WO    WO-2020/261070   * 12/2020

*Primary Examiner* — Theodore J Stigell
(74) *Attorney, Agent, or Firm* — Corner Counsel, LLC

(57) ABSTRACT

A manual intraosseous (IO) device for introducing a bone portal to a predetermined depth relative to a surface of a target bone, and methods for using same. The device is manually actuated and configured to limit the depth of penetration of a bone portal into a bone cortex independently of an applied driving force and independently of subcutaneous tissue thickness surrounding the bone cortex, while providing terminal feedback that the bone portal has been penetrated to the predetermined depth. The device has transfusion facilitating components that remain fixed at the penetration site following penetration of the bone portal to the predetermined depth and releasable components that are separated from the transfusion facilitating components prior to a transfusion operation. The device may also include a stabilizer, or base, that allows a health practitioner to easily locate the insertion site and allows low profile fixation of the IO transfusion component (IOcatheter).

20 Claims, 31 Drawing Sheets

(52) U.S. Cl.
CPC ............... *A61B 2017/3407* (2013.01); *A61B 2017/3492* (2013.01)

(58) Field of Classification Search
CPC ............ A61B 2017/3492; A61B 50/30; A61B 2090/08021; A61B 2090/0811
See application file for complete search history.

(56) References Cited

U.S. PATENT DOCUMENTS

| | | |
|---|---|---|
| 8,328,738 B2 | 12/2012 | Frankhouser et al. |
| 9,173,679 B2 | 11/2015 | Tzachar et al. |
| 12,004,776 B2 * | 6/2024 | Swisa ................. A61B 10/025 |

* cited by examiner

MANUAL INTRAOSSEOUS DEVICE AND METHOD FOR INTRODUCING A BONE PORTAL TO A PREDETERMINED DEPTH IN A BONE

RELATED APPLICATIONS

This is a continuation application of U.S. patent application Ser. No. 18/280,767, filed on Sep. 7, 2023, now U.S. Pat. No. 12,004,776, issued on Jun. 11, 2024, which is a 371 National Stage Entry of PCT/IB22/55857, filed on Jun. 24, 2022, which claims priority to Israeli Patent Application No. 284380, filed Jun. 24, 2021, the disclosures of which are incorporated herein by reference in their entirety.

FIELD OF THE INVENTION

The present invention relates to the field of intraosseous devices. More particularly, the invention relates to a manual intraosseous device and method for introducing a bone portal to a predetermined depth relative to a bone surface in order to reliably and safely access the bone marrow cavity.

BACKGROUND OF THE INVENTION

The administration of medication to an injured or critically ill patient is many times delayed due to the difficulty in establishing an intravenous line. During such situations, a lifesaving alternative by which vascular access is quickly achieved is through intraosseous (IO) infusion, whereby fluids and medications are injected into a marrow cavity of a long bone such as the femur, tibia and humerus, or of the sternal bone in the manubrium. Fluids drain into a central venous canal and is then carried to the bloodstream.

The success of an IO infusion procedure is contingent upon penetration of the bone cortex to a patient-specific depth in order to access the bone marrow. The bone marrow will not be accessible if tissue overlying a target bone is not sufficiently penetrated, for example when an incorrect needle length is employed or an excess amount of subcutaneous tissue exists, or alternatively if the needle is deployed to an excessive depth, resulting in possible damage to healthy surrounding tissues and organs when the bone is overpenetrated after the needle has penetrated two opposite diametric regions of the bone.

Particularly, the bones of infants are very thin and are sometimes concealed by excessive overlying soft tissue. A health practitioner performing an IO penetration procedure therefore requires a high level of accuracy to determine the proper depth of penetration for the IO needle.

Penetration of the sternum, for example, presents a high risk in overpenetration of its manubrium, which is joined to the clavicles and the cartilages of the first pair of ribs, due to the relatively thin marrow cavity of the sternum. A needle that unintentionally penetrates the distal cortex of the manubrium is liable to injure vital body parts such as the heart, lungs and the great vessels associated with the heart.

Bones having a thicker wall than the sternum, such as long bones in adults, are also subject to overpenetration if the health practitioner applies an excessive penetration force, which may continue to be applied even after the needle has accessed the bone cavity.

It would be desirable to provide an IO device for preventing deeper, potentially harmful penetration after the health practitioner has introduced the bone portal to a predetermined depth within a bone cortex.

Some prior art IO devices are known to limit penetration; however, they do not provide an indication to the health practitioner that the bone portal has been introduced to the predetermined depth, and consequently the health practitioner often continues to apply a penetrating force. In addition to the unnecessary effort that is being exerted, the continuously or excessively applied penetrating force transmitted to the intraosseous needle caused to be stationary is liable to injure surrounding body structures and even lead to a bone fracture in the vicinity of the penetration site.

SUMMARY OF THE INVENTION

One aspect of the invention is a manual intraosseous device for introducing a bone portal to a predetermined depth relative to a surface of a target bone, comprising an intraosseous catheter configured with a bone portal that is penetrable into a cortex of the target bone; a releasable component assembly that is releasably attached to the intraosseous catheter, by which a manual axial force is transmittable to the intraosseous catheter to initiate corresponding axial penetration into subcutaneous tissue associated with the target bone as well as into the cortex of the target bone; and a penetration depth limiting mechanism comprising at least first and second elements provided with the component assembly that are separate from each other when the bone portal is penetrated within the bone cortex by less than a predetermined depth relative to an outer surface of the bone cortex which is independent of a thickness of the subcutaneous tissue and are secured to each other when the bone portal is penetrated within the bone cortex to the predetermined depth, to prevent any additional distal displacement of the bone portal. The penetration depth limiting mechanism is a terminal feedback indicating mechanism which is configured to provide a tactile indication that the intraosseous catheter is either proximally or distally displaceable following application of the manual axial force in a corresponding direction when the bone portal is penetrated within the bone cortex by less than the predetermined depth and that the intraosseous catheter is prevented from undergoing proximal or distal displacement after the bone portal has been penetrated within the bone cortex to the predetermined depth despite application of the manual axial force. The intraosseous catheter is further configured with an internal lumen through which an infusion liquid or a bone marrow aspirate is flowable, and at least one port by which the internal lumen is positionable in fluid communication with a bone marrow cavity of the target bone, and is connectable with a connector interface that induces flow of the infusion liquid or the bone marrow aspirate when the component assembly is released from the intraosseous catheter.

Another aspect of the invention is a manual intraosseous device for introducing a bone portal to a predetermined depth relative to a surface of a target bone, comprising an intraosseous catheter configured with a driving member and a bone portal that is penetrable into a cortex of the target bone in conjunction with the driving member; a driving member hub configured to carry the intraosseous catheter; an inner tubular sleeve; an outer tubular sleeve concentric to, and axially displaceable relative to, the inner sleeve; detachable connection means for releasably connecting the intraosseous catheter hub from the outer sleeve member, by which a manual axial force applied to the driving member hub is transmittable to the intraosseous catheter to initiate corresponding axial penetration into subcutaneous tissue associated with the target bone as well as into the cortex of the target bone; and a penetration depth limiting mechanism comprising at least first and second elements provided with the inner sleeve and outer sleeve, respectively, which are separate from each other when the bone portal is penetrated within the bone cortex by less than a predetermined depth relative to an outer surface of the bone cortex which is independent of a thickness of the subcutaneous tissue and are secured to each other when the bone portal is penetrated within the bone cortex to the predetermined depth, to prevent any additional distal displacement of the bone portal. The intraosseous catheter is further configured with an internal lumen through which an infusion liquid or a bone marrow aspirate is flowable, and at least one port by which the internal lumen is positionable in fluid communication with a bone marrow cavity of the target bone, and is connectable with a connector interface that induces flow of the infusion liquid or the bone marrow aspirate when the driving member hub is released from the intraosseous catheter.

Another aspect of the invention is a stabilizer for an intraosseous device, comprising a base configured to be affixed to a skin surface and to be detachably coupled with a structure of the intraosseous device, wherein the base is bored with an aperture that is adapted to overlie a penetration site and receive a needle assembly of the intraosseous device; and a surface surrounding the base which is configured with a plurality of guidable peripheral edges. Each of the guidable edges has a distinctive shape that facilitates positioning close to a prominent anatomical feature and that is located at a predefined age-specific or site-specific distance from the aperture.

Another aspect of the invention is a combination of a stabilizer for an intraosseous device and a flexible transfusion tube, comprising a base configured to be affixed to a skin surface and to be detachably coupled with a structure of the intraosseous device, wherein the base is bored with an aperture that is adapted to overlie a penetration site and receive a needle assembly of the intraosseous device for use during a penetration operation, and is additionally formed with a plurality of differently oriented notches; and a flexible tube removably connected to the needle assembly and within a lumen of the flexible tube a solid driving member is insertable during the penetration operation, wherein the flexible tube, following removal of the driving member therefrom, is in fluid communication with a connector interface that induces flow of infusion liquid or bone marrow aspirate during a transfusion operation. The flexible tube is securable in one of the notches during the transfusion operation to facilitate secured connection to the base interface.

Another aspect of the invention is a method for accessing a bone marrow cavity, comprising the steps of pinpointing a prominent anatomical landmark associated with a suitable penetration site; aligning a guidable edge of a stabilizing base configured with a predetermined geometrical relation between the guidable edge and an aperture bored in the base which is adapted to overlie the penetration site, with the prominent anatomical landmark; applying a manual axial force by an intraosseous device body that causes an intraosseous catheter attached therewith to be introduced through the aperture and to penetrate a cortex of a target bone, until the intraosseous catheter has been penetrated to a predetermined depth relative to a surface of the target bone that ensures access of the intraosseous catheter to a bone marrow cavity of the target bone, wherein additional distal penetration of the intraosseous catheter is prevented despite additional application of distal manual axial force by the intraosseous device after the intraosseous catheter has been penetrated to the predetermined depth; and detaching the intraosseous device body from the intraosseous catheter and base, fixation of the intraosseous catheter to built-in notch in the base to allow a low profile fixation of the tube and a secure fluid transport from and to the bone Yet another aspect of the invention is a manual intraosseous device for introducing a bone portal to a predetermined depth relative to a surface of a target bone, comprising: an intraosseous needle assembly including an intraosseous catheter configured to facilitate transfusion of fluids and aspiration of bone marrow and having a bone portal adapted to penetrate into subcutaneous tissue adjacent the target bone and the cortex of the target bone and a flexible tube through which liquids can be conveyed to and from the bone marrow of the target bone, and a driving member releasably attached to the intraosseous catheter and by which a manual axial force is transmittable to the intraosseous catheter to initiate axial penetration into the subcutaneous tissue and cortex of the target bone; an inner tubular sleeve arranged concentric to the intraosseous catheter; an outer sleeve member including an outer sleeve arranged concentric to the inner sleeve and being axially displaceable relative to an outer surface of the inner sleeve and a grip engaging an outer surface of outer sleeve, the outer sleeve member operably connected to the driving member, and wherein the driving member includes a rod and a driving member hub engaging the outer sleeve member and having a throat portion receiving a proximal end of the rod therein; a probe needle assembly engaged with the outer sleeve member and at least partially received within an interior of the inner sleeve, and including at least one bone cortex-contacting probe needle, a motion inducer and an annular needle holder securing the at least one probe needle therein; a proximal spring positioned within the outer sleeve member, operably connected to the probe needle assembly, and configured to limit the depth that bone portal penetrates the target bone; and a distal spring positioned within the inner sleeve, operably connected to the probe needle assembly, and configured to move the outer sleeve member to a starting position if the bone portal penetrates the target bone cortex to the predetermined depth, to prevent any additional distal displacement of the bone portal. The proximal and distal springs provide a terminal feedback indicating mechanism configured to provide a tactile indication that the intraosseous catheter is either proximally or distally displaceable following application of the manual axial force in a corresponding direction when the bone portal penetrates the bone cortex by less than the predetermined depth and that the intraosseous catheter is prevented from undergoing proximal or distal displacement after the bone portal has penetrated the bone cortex to the predetermined depth despite application of the manual axial force.

Still another aspect of the invention is a manual intraosseous device for introducing a bone portal to a predetermined depth relative to a surface of a target bone, comprising: an intraosseous catheter configured with a driving member and a bone portal that is penetrable into a cortex of the target bone in conjunction with the driving member; a driving member including a driving member hub configured to support the intraosseous catheter; an inner tubular sleeve; an outer tubular sleeve concentric to, and axially displaceable relative to, the inner sleeve; wherein the driving member hub is connected to the outer sleeve, by which a manual axial force applied to the driving member hub is transmittable to the intraosseous catheter to initiate corresponding axial penetration into subcutaneous tissue associated with the target bone and into the cortex of the target bone; and a penetration depth limiting mechanism comprising at least first and second elements provided within the inner sleeve and outer sleeve, respectively, which are separate from each other when the bone portal is penetrated within the bone cortex by less than a predetermined depth relative to an outer surface of the bone cortex which is independent of a thickness of the subcutaneous tissue and are secured to each other when the bone portal is penetrated within the bone cortex to the predetermined depth, to prevent any additional distal displacement of the bone portal.

It is an object of the present invention to provide a manual intraosseous device that reliably limits the depth relative to a bone surface to which a bone portal is introduced regardless of the magnitude of force that is applied and of the thickness of subcutaneous tissue.

It is an object of the present invention to provide a manual intraosseous device for introducing a bone portal to a predetermined depth relative to a bone surface that can be withdrawn in its entirety from the tissue if the bone cortex has not been penetrated at all or if the bone portal has not been introduced to the predetermined depth within the marrow cavity.

It is an additional object of the present invention to provide a manual intraosseous device capable of generating a reliable indication that the bone portal has been introduced to the predetermined depth and that the health practitioner should stop applying the penetrating force.

Other objects and advantages of the invention will become apparent as the description proceeds.

BRIEF DESCRIPTION OF THE DRAWINGS

Embodiments of the invention are further described but are in no way limited by the following illustrations.

DETAILED DESCRIPTION OF THE INVENTION

The manually actuated intraosseous (IO) device is configured to limit the depth of penetration of a bone portal into a bone cortex independently of an applied driving force and independently of subcutaneous tissue thickness surrounding the bone cortex, while providing terminal feedback that the bone portal has been penetrated to the predetermined depth. The IO device has transfusion facilitating components that remain fixed at the penetration site following penetration of the bone portal to the predetermined depth and releasable components that are separated from the transfusion facilitating components prior to a transfusion operation. In some embodiments, the device may also include a stabilizer, or base, that allows a health practitioner to easily locate the insertion site and allows low profile fixation of the IO transfusion component (IO catheter).

As referred to herein, a "transfusion" operation is meant to include both infusion of liquids into the bone marrow cavity and aspiration of bone marrow from the bone marrow cavity.

Figure 1:
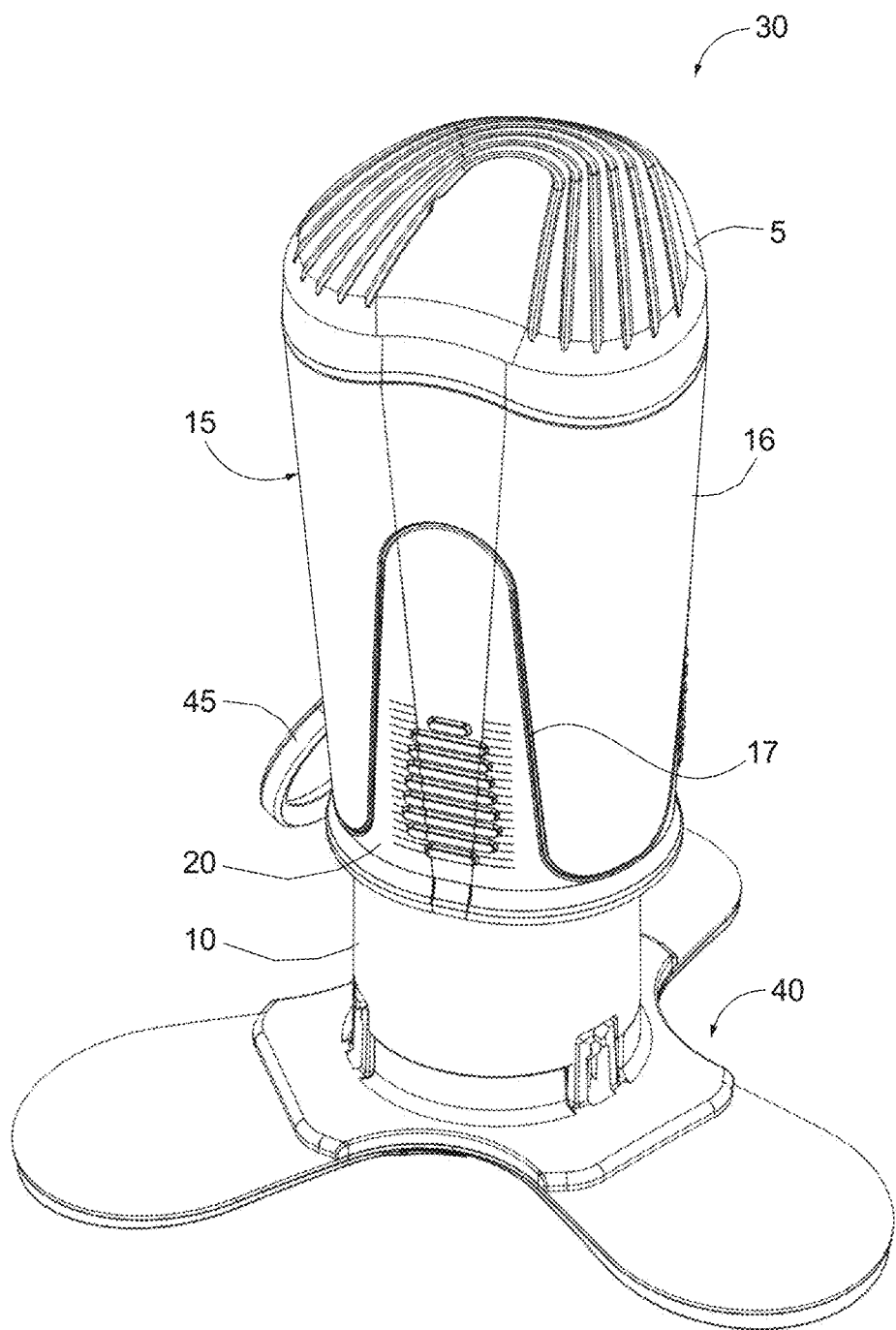
FIG. 1 is a top perspective view of an assembled manual IO device according to a first embodiment of the present invention.

FIG. 1 illustrates an assembled manually actuated IO device 30 prior to penetration into a target bone, according to a first embodiment. The IO device 30 comprises an inner tubular sleeve 10, and an outer tubular sleeve 20 concentric to inner sleeve 10 and carrying a probe needle assembly arranged such that the outer sleeve 20 is axially displaceable relative to the outer tubular surface of inner sleeve 10, i.e., in a direction parallel to the axis of a main intraosseous needle assembly adapted to penetrate into adjoining tissue and to facilitate transfusion of life-saving fluids and aspiration of bone marrow. A grip 16, such as one configured with a cutout 17, e.g., of an inverted U-shape, may be integrally formed with the outer surface of outer sleeve 20 to assist in gripping the handle while pushing it in the proximal direction to axially displace it relatively to inner sleeve 10. The combination of grip 16 and outer sleeve 20 defines an outer sleeve member 15. In other words, the outer sleeve member 15 constitutes a "handle" of the device 30 that includes the outer sleeve 20 and grip 16 (and in one embodiment also includes the inner part of outer sleeve 20). The addition of grip 16 increases the lateral dimension of the outer sleeve member 15 so that the latter is able to assume a non-circular cross section, although a circular cross section is also within the scope of the invention.

Various elements and embodiments of the IO device 30 will now be discussed.

Figure 1A:
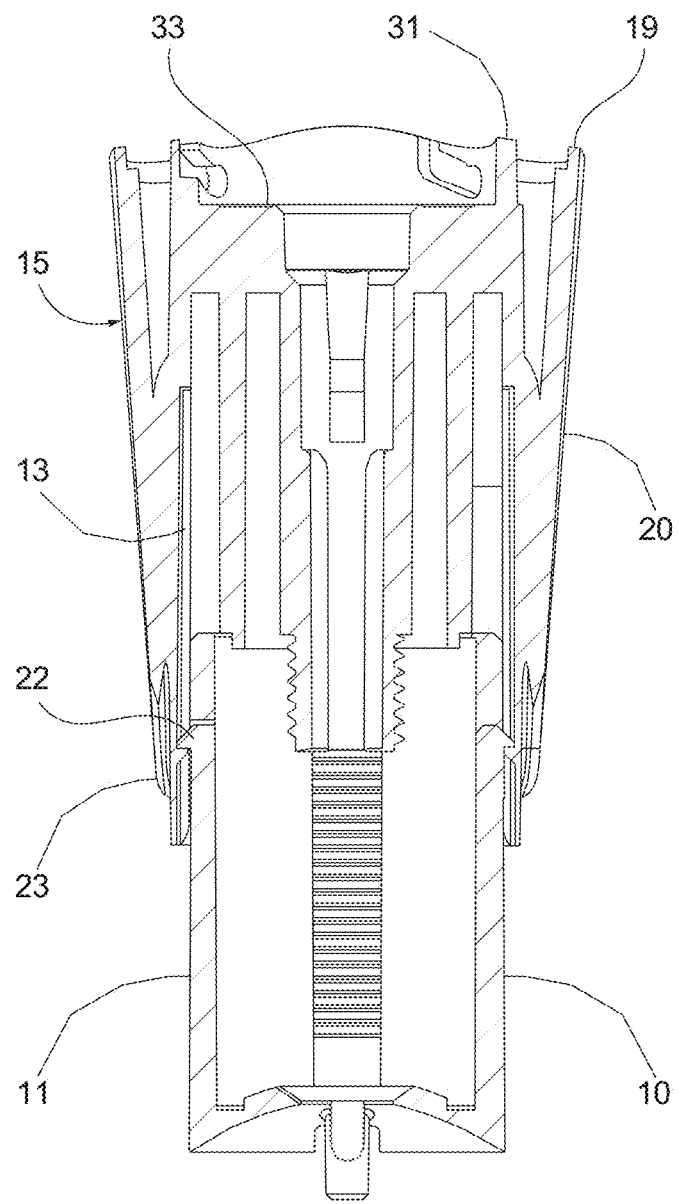
FIG. 1A is a cross-sectional view of components of the device of FIG. 1.

In one embodiment outer sleeve 20 includes a solid internal structure (also referred to as outer tubular sleeve 20). In one such embodiment, outer sleeve 20 includes an inner structure to be assembled with inner sleeve 10, as shown in FIG. 1A. In another embodiment, outer sleeve 200 includes a separate inner part, referred to herein as a body 4, that is assembled into outer sleeve 200 (i.e., outer sleeve 200 is assembled onto body 4) as described hereinbelow and shown in FIGS. 1B and 1C.

FIG. 1A is an axial cross-sectional view showing one embodiment in which outer sleeve 20 is one solid part with an inner structure. To ensure that inner sleeve 10 and outer sleeve 20 remain in a mutual concentric relation during axial displacement, a protrusion 22, e.g., with a pointed end, protruding radially outwardly from outer surface 11 of inner sleeve 10 is received in an axial slot 13 formed in the inner surface of outer sleeve 20, as shown in FIG. 1A. In some embodiments, two diametrically opposite slots 13 are provided, each configured to receive a corresponding protrusion 22 therein. Outer sleeve 20 may include a stopper 23 protruding inwardly from the inner surface of outer sleeve 20, located distally to the distal end of slot 13, to limit the proximal displacement of outer sleeve 20 relative to inner sleeve 10. Both the distal edge of protrusion 22 and the proximal edge of stopper 23 may be planar to improve the engagement therebetween.

Figure 1B:
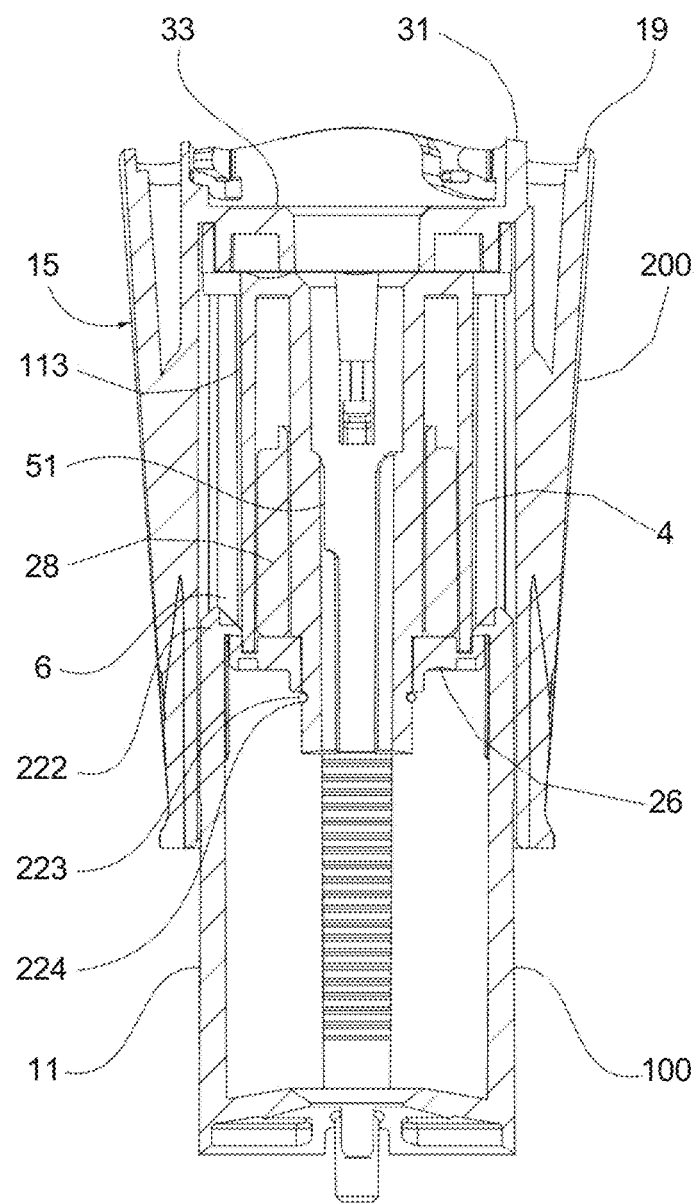
FIG. 1B is a cross-sectional view of components of a manual IO device according to a second embodiment of the present invention.

FIG. 1B illustrates another embodiment in which outer sleeve 200 is assembled onto body 4 to form outer sleeve member 15. The engagement between inner sleeve 100 and outer sleeve member 15 is carried out by means of additional elements as will be described hereafter and shown in FIGS. 1B and 1C.

Body 4 includes an annular mounting post 51 protruding outwardly from an outer surface of body 4. A motion inducer 28 is inserted through annular mounting post 51 of body 4 while snaps 77 of motion inducer 28 (see FIG. 7) aligned to slots in the body 4 and reach its final position on the body 4 when slots become an open tunnel (i.e., are in fully open positions). In some embodiments, this is an undetachable connection.

In some embodiments, an annular needle holder 26 is also inserted through annular mounting post 51, and these two elements have a similar diameter (ID and OD, respectively) so that there is a friction between the two elements that holds them connected (i.e., an interference or friction fit). To strengthen the connection between these two parts, further connecting means may be included in some embodiments (i.e., in addition to a friction fit). Non-limiting examples of further connecting means may include snaps or pins that are received in corresponding channels or apertures, or a c-clips that prevent (distal) movement of annular needle holder 26.

Figure 1C:
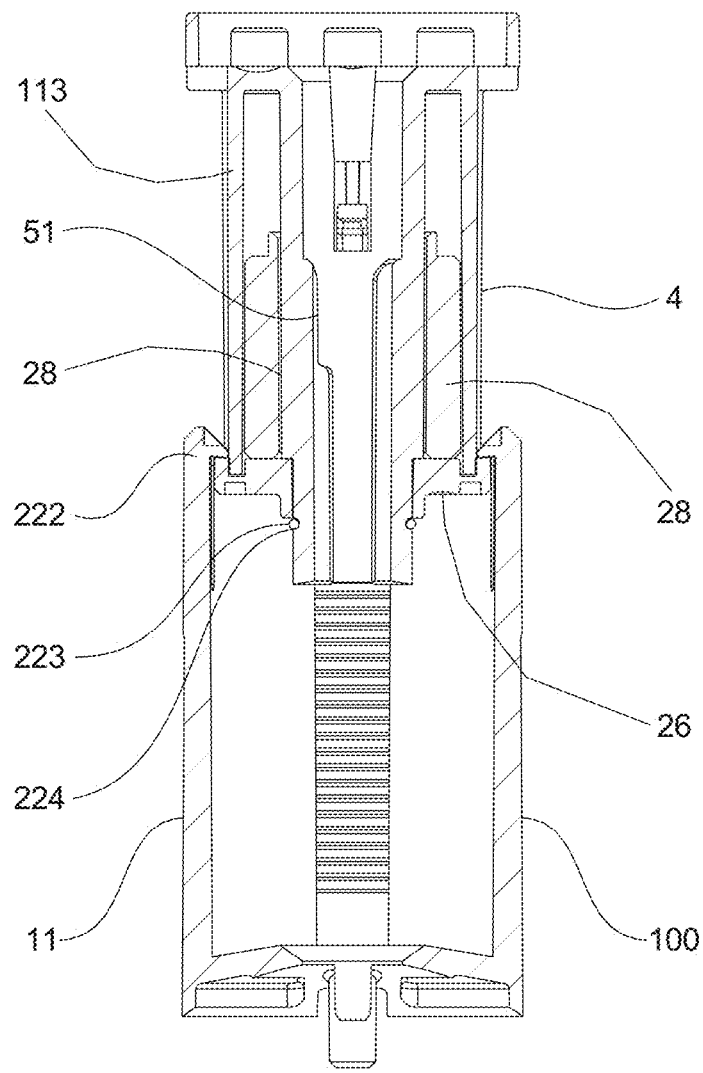
FIG. 1C is another cross-sectional view of components of the device of FIG. 1B.

In the embodiment shown in FIGS. 1B and 1C, c-clip 223 is inserted on to annular mounting post 51 of body 4 and to the final position inside slot 224, and thereby prevents detachment of inner sleeve 100 from body 4.

To ensure that inner sleeve 100 and body 4 remain in a mutual concentric relation during axial displacement, a protrusion 222, e.g., with a pointed end, protruding radially inwardly from outer surface 111 of inner sleeve 100 is received in an axial slot 6 formed between the outer surface of body 4 and the inner surface of outer sleeve 200. In some embodiments, two or more ribs 113 protrude outwardly from outer surface 111 of inner sleeve 100 are received in axial slots formed in the inner surface of outer sleeve 200.

Annular needle holder 26 is inserted through mounting post 51 protruding in outwardly from the inner surface of body 4 to limit the proximal displacement of body 4 relative to inner sleeve 100. To improve the engagement therebetween, both the distal edge of protrusion 222 and the proximal surface of needle holder 26 may be planar.

Outer sleeve member 200 is mounted onto body 4 and thereby that prevents outwardly movement of protrusion 222. Outer sleeve member 200 and body 4 are connected in an undetachable connection by means of screws, snaps, or any other similar means.

Referring again to FIGS. 1 and 2, a driving member hub 5 configured to support (i.e., carry) an IO needle assembly 35 is provided in an abutting relation with a proximal surface of the outer sleeve member 15. Driving member hub 5 may be configured with a domed proximal surface and with the same non-circular horizontal cross section as the outer sleeve member 15 and aligned therewith to improve a user's grip thereof. The distal end of inner sleeve 10 in turn is coupled with a stabilizer 40 through which the probe needles and tube assembly pass when penetrating the patient's underlying tissue.

Outer sleeve member 15 is distally displaceable relative to inner sleeve 10 or 100 when a manual force is applied to driving member hub 5, but is prevented from being displaced due to unintentional operation of IO device 30 when a safety latch 45 is coupled between outer sleeve 20 and inner sleeve 10 or outer sleeve 200 and inner sleeve 100. In various embodiments, safety latch 45 may be configured with a finger-engageable ring and one or more coupling elements that are connected to the ring and pass through both inner sleeve 10, 100 and outer sleeve 20, 200 respectively, via aligned apertures, or may be configured in other ways well known to those skilled in the art.

Safety latch 45 may be releasably coupled to inner sleeve 10, 100 and outer sleeve 20, 200, or alternatively may be undetachably but movably connected to one of inner sleeve 10, 100 or outer sleeve 20, 200.

It will be appreciated that in alternate embodiments, IO device 30 may be provided without various components shown/described herein, e.g., the alignment protrusions, without a stabilizer and/or without a safety latch.

Figure 3:
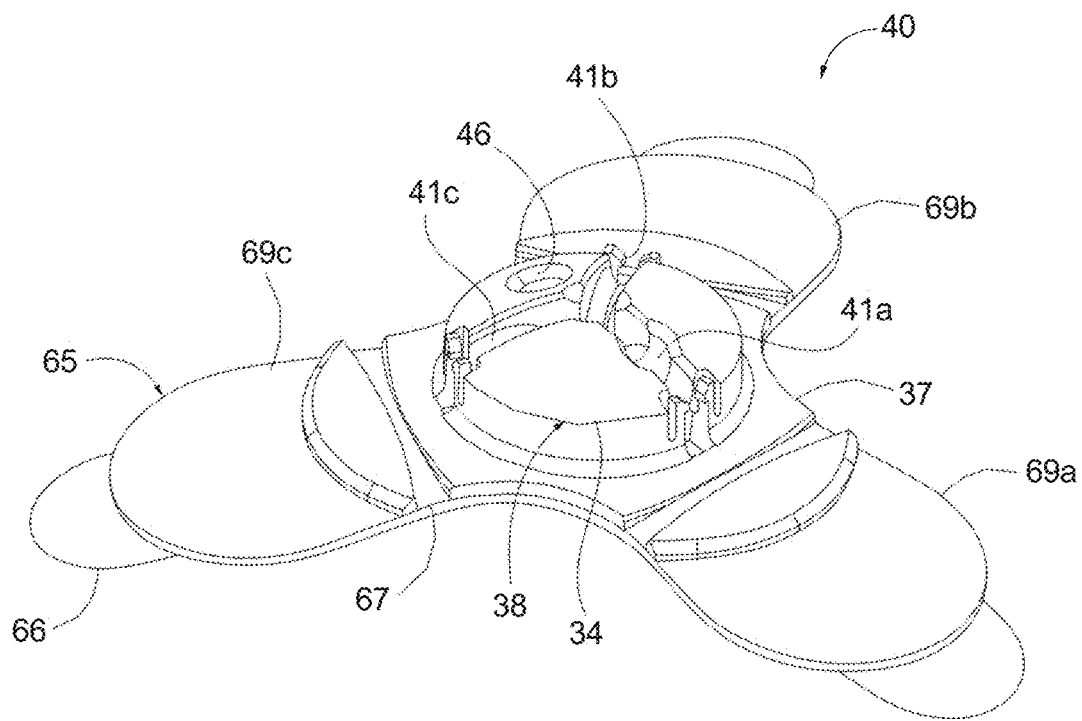
FIG. 3 is top perspective view of a stabilizer and related elements according to an embodiment of the present invention for use with the manual IO devices of the present invention.

Stabilizer 40 is adapted to be affixed to a skin surface during both a penetration operation and a transfusion operation. Inner sleeve 10 or 100 is adapted to be coupled to stabilizer 40 during a penetration operation and decoupled therefrom in response to a user action once the bone portal has been introduced to the predetermined depth within the bone. Stabilizer 40, as shown in FIGS. 3/3A and 4/4A, is further discussed below.

Figure 2:
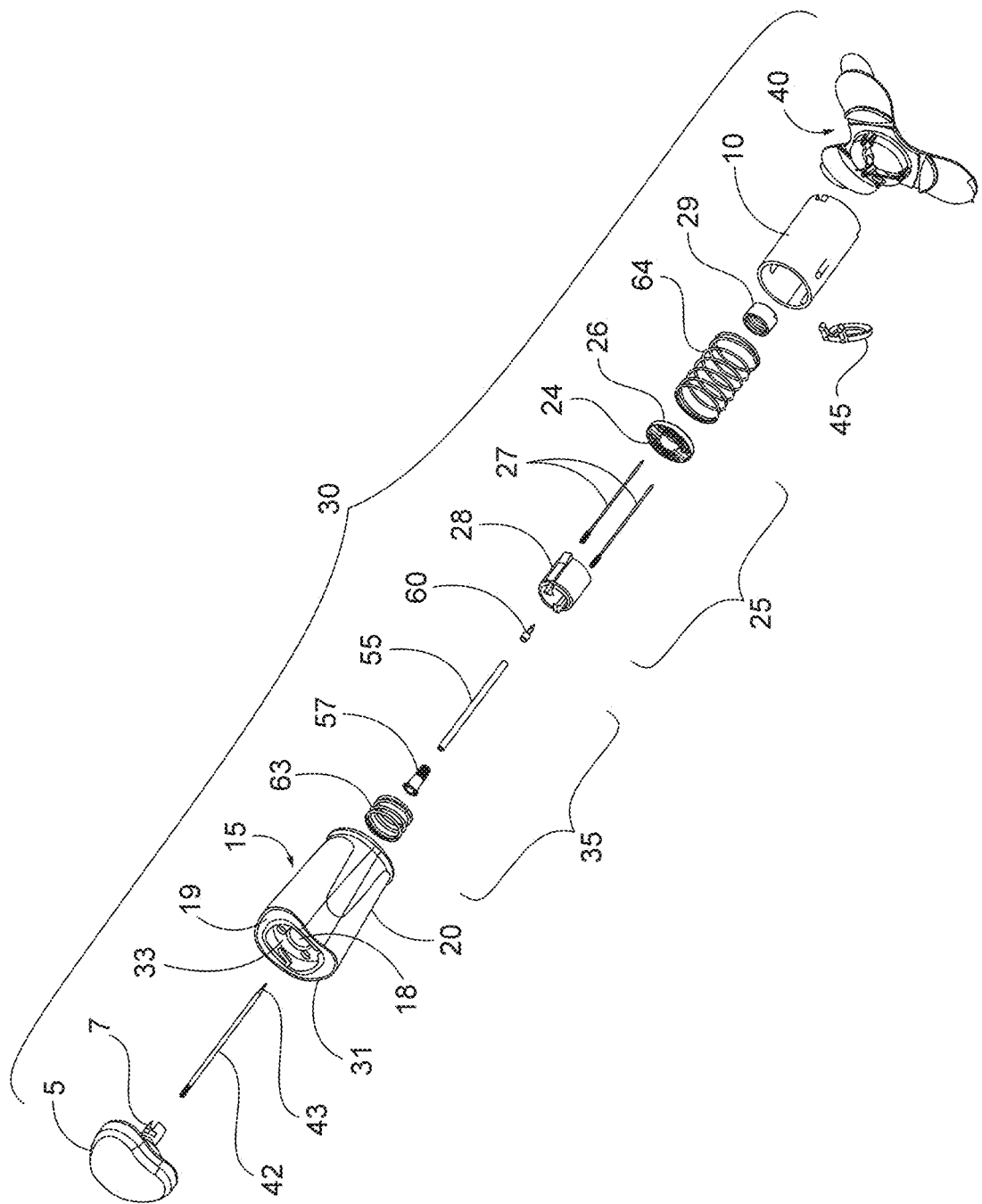
FIG. 2 is an exploded view of the device of FIGS. 1 and 1A.

With reference to FIG. 2, driving member hub 5 is shown to be separated from outer sleeve member 15. Driving member hub 5 may be detachably coupled with outer sleeve member 15, or alternatively may be undetachably connected to outer sleeve member 15 for one-time use embodiments of the IO device 30. A proximal surface 19 of outer sleeve member 15 is adapted to be in abutting relation with an undersurface of driving member hub 5 that surrounds a cavity (i.e., a central opening) 18 provided within the outer sleeve member 15. A wall 31 delimiting the cavity extends from the radial outward edge of an annular intermediate surface 33 of the outer sleeve member 15, which is distally spaced from proximal surface 19, to a terminal edge that is proximally spaced from proximal surface 19 (also shown in FIGS. 1A and 1B).

Figure 7:
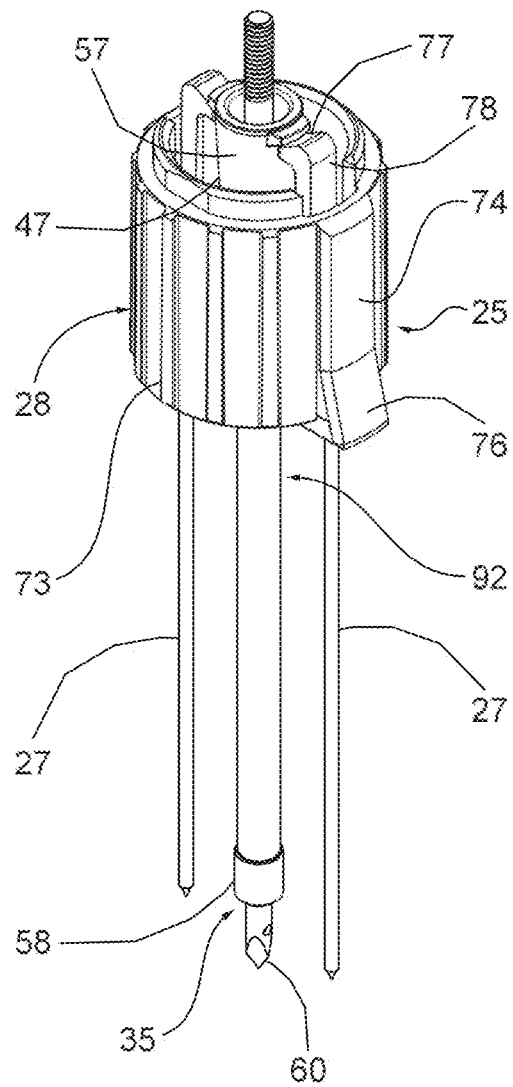
FIG. 7 is a top perspective view of components of the device of FIG. 1.
Figure 8:
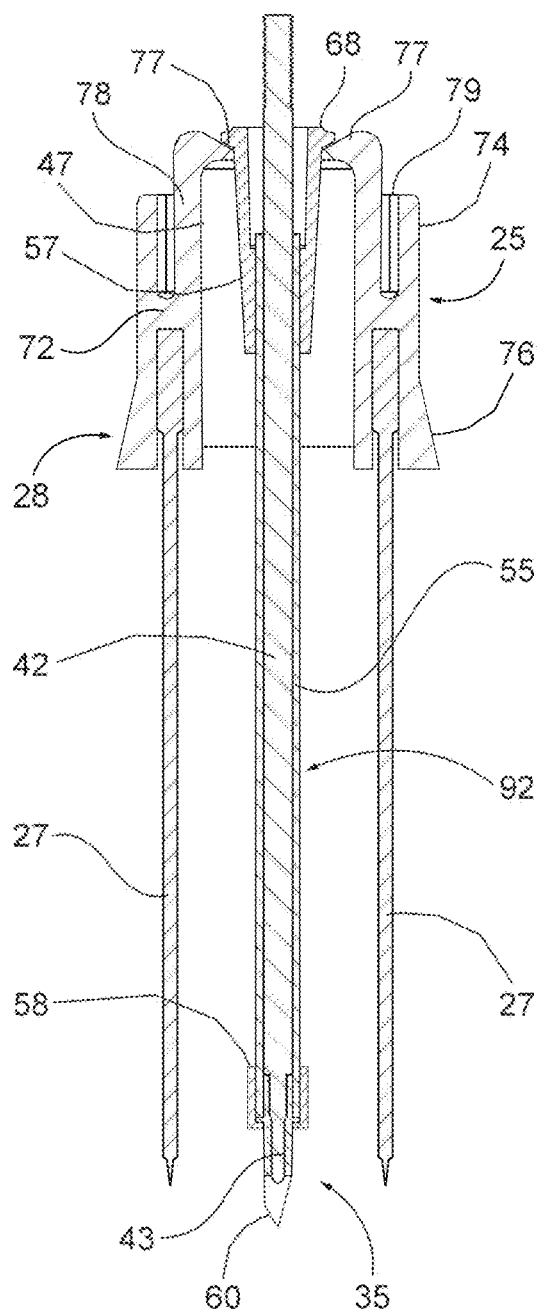
FIG. 8 is cross-sectional view of the components of FIG. 7.
Figure 10:
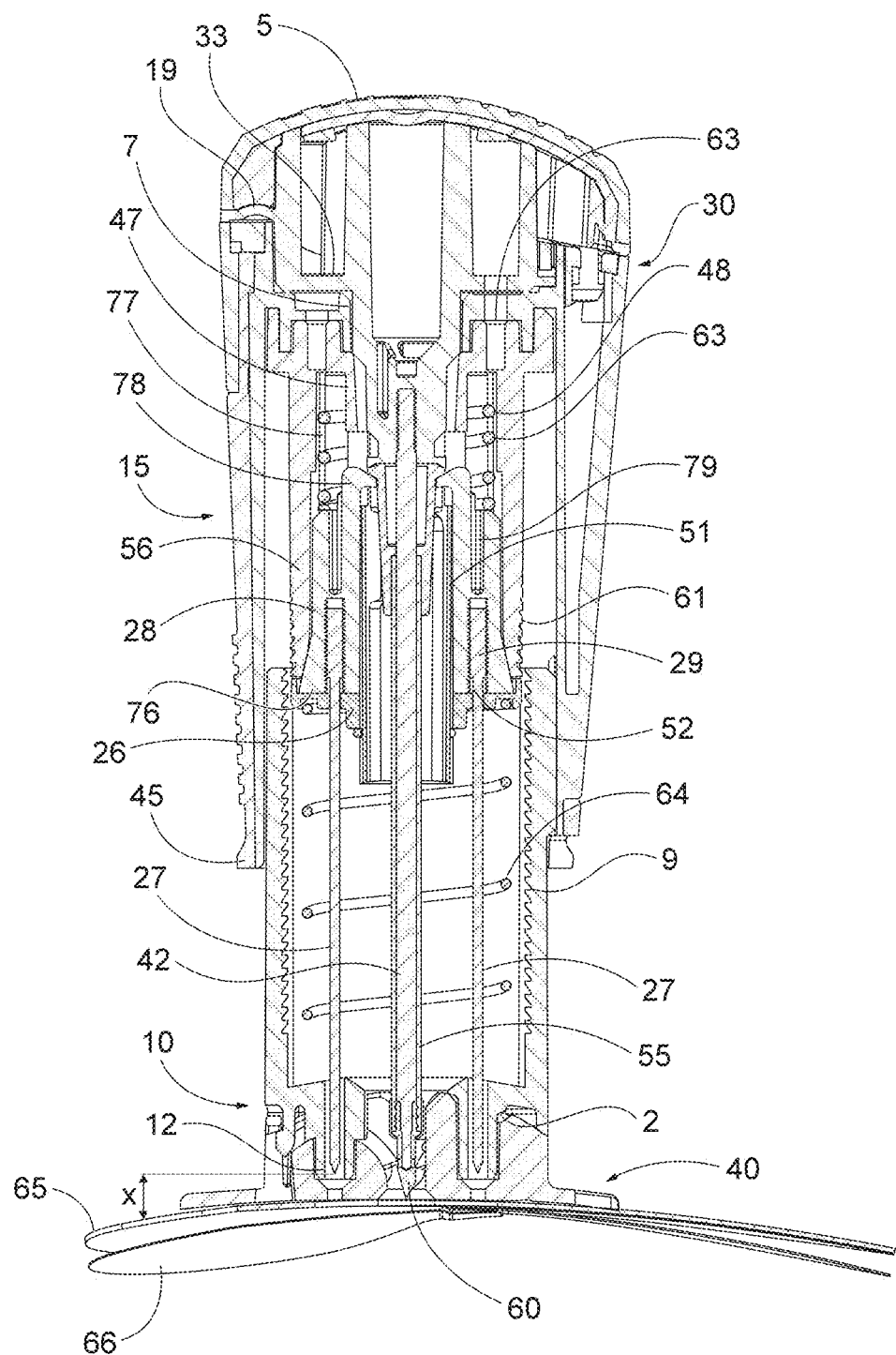
FIG. 10 is a pre-penetration cross-sectional view of the device of FIG. 1, as placed on a patient's skin for penetration into the patient's sternal bone cortex.

Reference is made to FIGS. 7, 8 and 10, which show a probe needle assembly 25 engaged internally with an element of outer sleeve member 15 (or with an element of body 4) and also partially received within the interior of inner sleeve 10, 100. Probe needle assembly 25 comprises an annular needle holder 26 to which one or more bone cortex-contacting probe needles 27 are secured via corresponding through-holes 24. These probe needles 27 are inserted into bores at the distal end of motion inducer 28 in an undetachable connection e.g., via threading, adhesive or other attachment means. The probe needles 27 pass through corresponding through-holes 24 of annular needle holder 26. The shank of each probe needle 27 may have a uniform thickness, or alternatively may be configured with a radial protrusion. For example, in some embodiments the radial protrusion may protrude radially by a distance of at least 0.2 mm from the shank peripheral surface and may be spaced by a distance of up to 1 cm from the probe end. In various embodiments, a motion inducer 28 and/or a nut 29 are also provided, with nut 29 secured to annular mounting post 51 to prevent unwanted movement of the motion inducer 28 (see FIGS. 2 and 10).

With further reference to FIGS. 2, 2A, 7 and 8, an intraosseous needle assembly 35 comprises an IO catheter 92 and a driving member. IO catheter 92 comprises a flexible tube 55 through which liquids can be conveyed to and from the bone marrow of a patient. The flexibility of tube 55 permits the tube to be folded after the penetration procedure is completed, to minimize tube protrusion from the patient's body. The proximal end of flexible tube 55 is connected to a female Luer-Lock fitting 57, which is adapted to be connected to a standard connector.

The driving member serves to transmit the manual force applied by the user to IO catheter 92 despite the flexibility of tube 55. In various embodiments, the driving member constitutes a rod 42 with a blunt distal end 43. Rod 42 is made of a metal (e.g., made of stainless steel). Rod 42 is received within the interior of tube 55, and the outer diameter of the rod may be substantially equal to the inner diameter of tube 55. In various embodiments, the proximal end of rod 42 is irremovably received, such as by frictional engagement, or removably received such as by threading, in an axial bore formed in a central throat portion 7 distally extending from driving member hub 5. Throat portion 7 in turn is received in a central opening 18 provided within the intermediate surface 33 of outer sleeve member 15, allowing the throat portion 7 to be securely engaged with the outer sleeve member 15. The function of throat portion 7 is both to firmly fix the rod 42 in place and to ensure stability during penetration of IO catheter 92 through the patient's soft subcutaneous tissue and into the underlying bone.

Figure 2A:
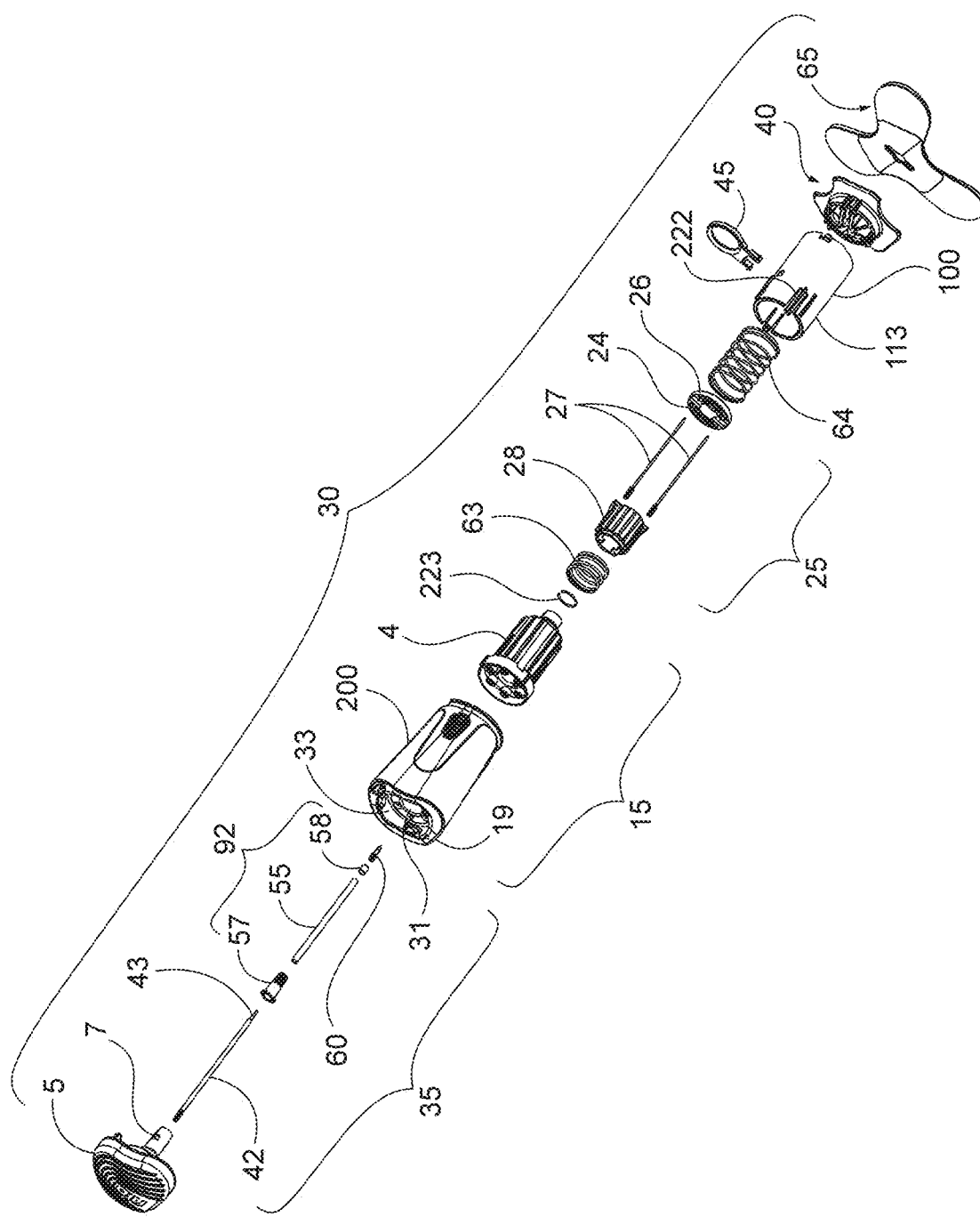
FIG. 2A is an exploded view of the device of FIG. 1B.

IO device 30 is resiliently displaceable by means of two compression springs 63 and 64 (see FIGS. 2 and 2A). Proximal spring 63 assists in limiting the depth of penetration of bone portal 60, as will be described hereinbelow. Distal spring 64 is instrumental in providing the terminal feedback by returning outer sleeve member 15 to a starting position if the bone portal 60 has not been deployed to a predetermined depth.

Reference is made again to FIGS. 3, 4 and 3A, 4A, which illustrate embodiments of stabilizer 40. Stabilizer 40 includes a thin and planar supporting surface 37 (e.g., made from polycarbonate or other type of rigid plastic), from which proximally protrudes a base 38 adapted to be detachably coupled with the inner sleeve 10. A thin fixation sticker 65 may be adhesively attachable to both a patient's skin surface adjoining the penetration site and to the distal side of supporting surface 37. In various embodiments, adhesive is generally applied onto both sides of fixation sticker 65, and a release liner (i.e., backing) 66 may be applied to the skin-facing side of fixation sticker 65 to protect the adhesive before use. In some embodiments, the adhesive is a pressure-sensitive adhesive.

Fixation sticker 65 may have three arms 69a-c extending in different directions from supporting surface 37 to increase the available surface area for connection of fixation sticker 65 to the patient's skin surface. The material of arms 69a-c may also extend radially inwardly to underlie, and to be integral with, supporting surface 37, and a foldable weakened area 67 may be provided between supporting surface 37 and a corresponding arm. In some embodiments, arms 69a-c have an equal shape and/or size. In other embodiments, their shape and/or size of each of arms 69a-c differ from each other.

Figure 3A:
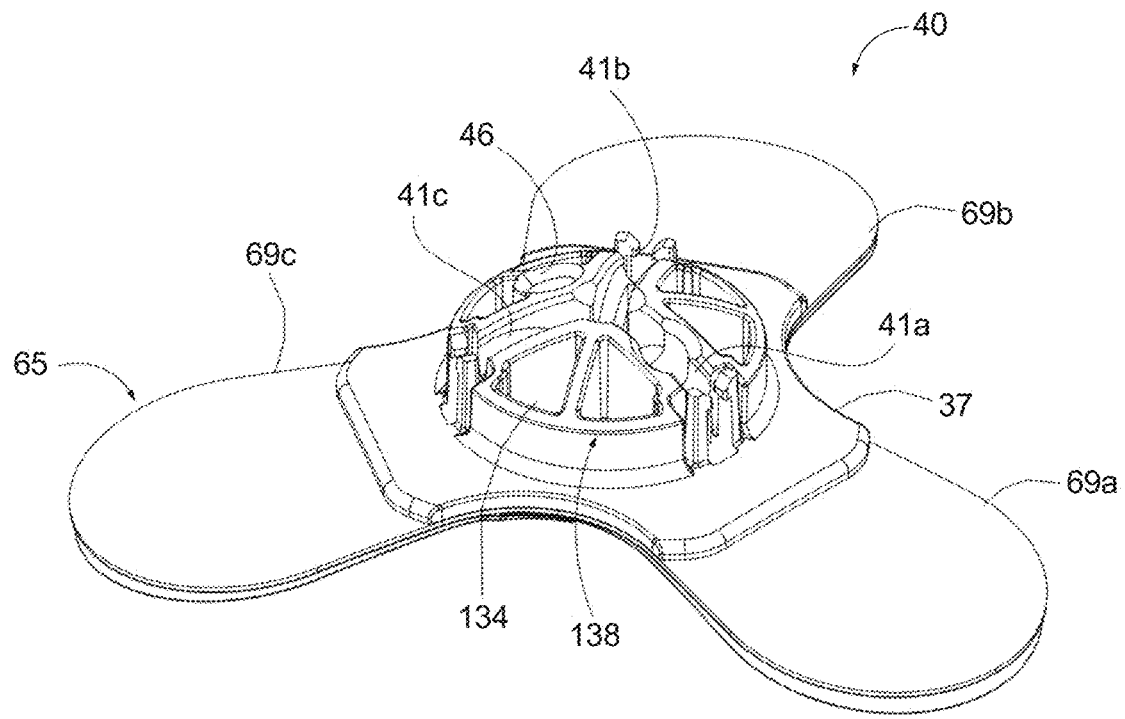
FIG. 3A is top perspective view of a stabilizer and related elements according to another embodiment of the present invention for use with the manual IO devices of the present invention.
Figure 4:
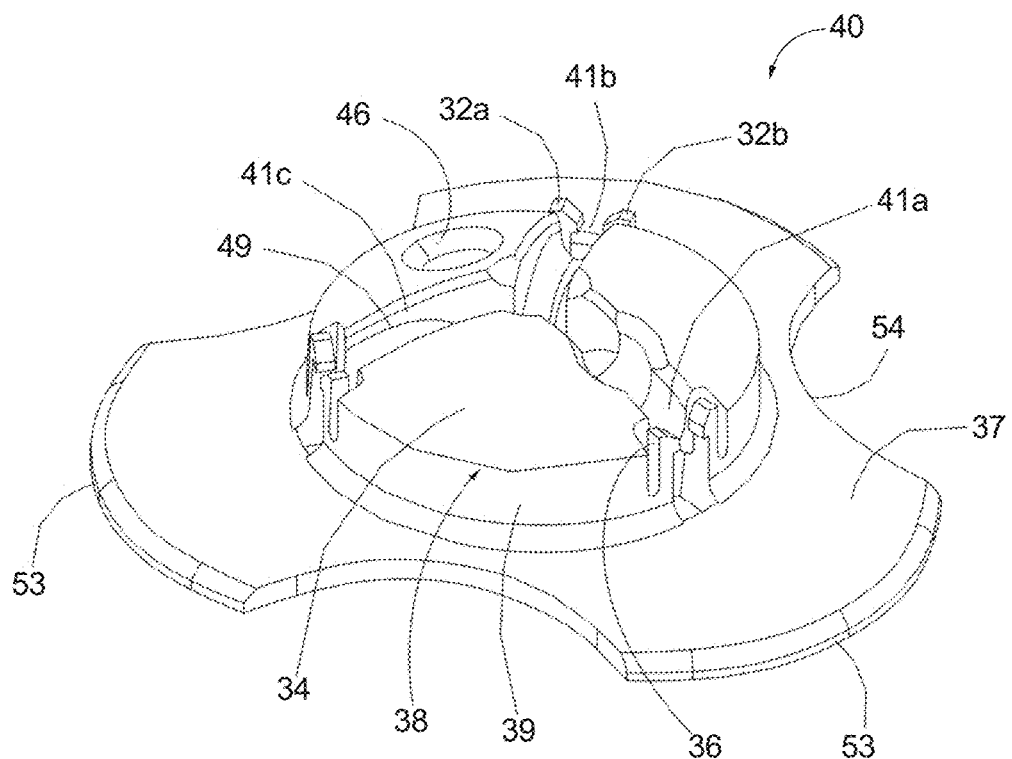
FIG. 4 is detailed top perspective view of the stabilizer of FIG. 3.
Figure 4A:
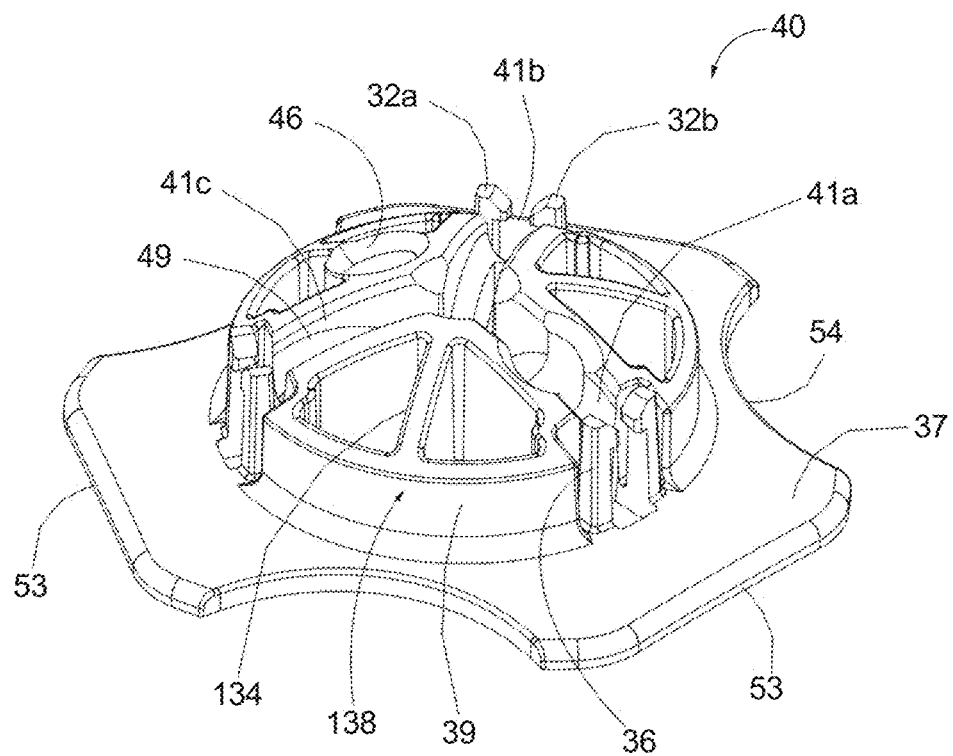
FIG. 4A is detailed top perspective view of the stabilizer of FIG. 3A.

In various embodiments, base 38 has a circular shape with a circumferential edge 39 substantially perpendicular to supporting surface 37 and a slightly domed proximal surface 34. In alternate embodiments, the base may have other shapes. In one embodiment, base 38 has a dome 34 with a solid/closed structure as shown in FIGS. 3 and 4. In another embodiment, base 138 has a dome 134 with a hollow/open structure as shown in FIGS. 3A and 4A, which reduces its weight and amount of material used to form same. Three notches 41a-c are formed within base 38, and radially extend from the center of base 38 to circumferential edge 39 to accommodate the passage therethrough of IO catheter 92. In alternate embodiments, notches 41a-c extend to circumferential edge 39 in another direction from a specific location on base 38.

One or more holes 46, each of which is bored in proximal surface 34, supporting surface 37 and in the underlying fixation sticker 65 surface and radially spaced from the center aperture of base 38, accommodates the passage therethrough of a corresponding probe needle 27.

Figure 15A:
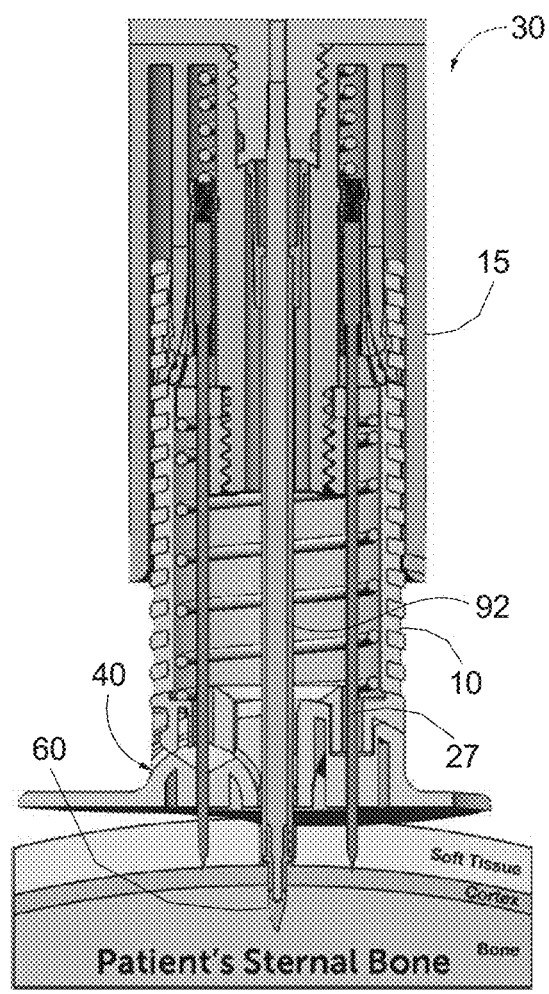
FIG. 15A is a cross-sectional view of the device of FIG. 1 with the distal end of IO needle assembly deployed to a predetermined and maximum depth within the patient's sternal bone cortex.
Figure 15B:
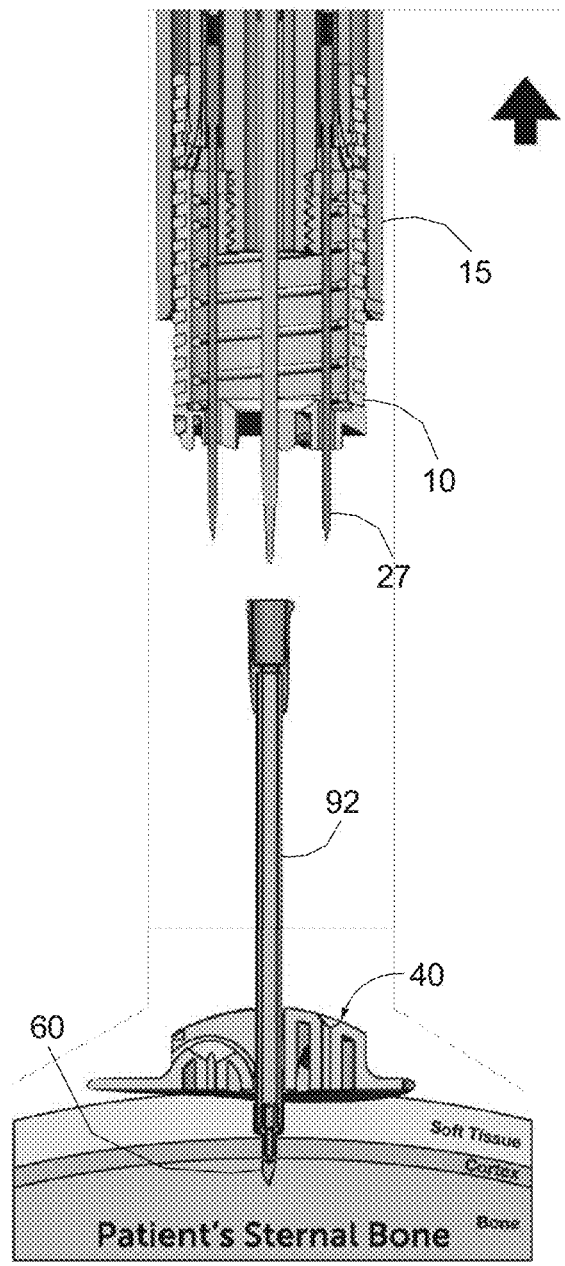
FIG. 15B is a cross-sectional view of the IO catheter penetrating the patient's sternal bone cortex with the releasable component assembly of the device of FIG. 1 having been pulled and proximally displaced away therefrom.
Figure 16:
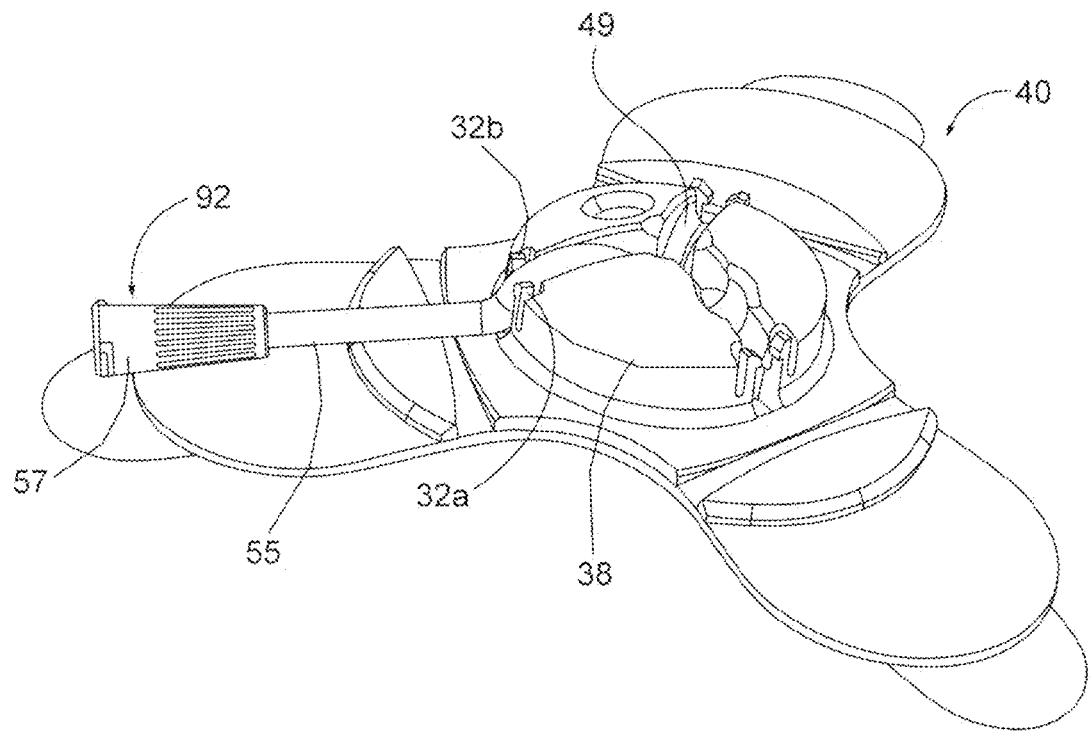
FIG. 16 is a top perspective view of the stabilizer of FIG. 3 with a flexible tube of the IO catheter secured in place therein.

One or more of the notches 41a-c may be configured with a curved supporting surface 49 proximally spaced from supporting surface 37 that curves distally from circumferential edge 39 to the center aperture of base 38, for supporting flexible tube 55 when it is bent during a transfusion operation (see FIGS. 15B and 16). Circumferential edge 39 may be configured with two opposed constricting elements 32a and 32b, or any other number of constricting elements, e.g., triangularly shaped, at each notch that reduce the width of the given notch in order to prevent unintentional movement of the affixed tube. Elements 32a-b also serve to couple with corresponding elements of the inner sleeve during a penetration operation.

In some embodiments, the notches 41a-c do not coincide with the center aperture of base 38, as long as the flexible tube 55 is able to be suitably bent and supported.

While the base 38 is shown having three notches 41a-c, any other number of notches may be formed within base 38 in alternate embodiments, including, but not limited to, one, two, four, five, six, seven or eight notches.

A portion 36 of base 38 adjoining the elongated back of each constricting element that does not protrude into a notch 41a, b or c protrudes from circumferential edge 39, to produce a socket, having for example a U-shape.

Planar supporting surface 37 has a plurality of terminal edges 53 that are spaced from and facing the corresponding notch 41a, b or c, and a plurality of guidable peripheral edges 54 extending between two adjacent terminal edges 53. In various embodiments, terminal edges 53 can be straight or convex. In some embodiments a terminal edge may be circumferentially spaced from a notch, producing a socket, or unaligned therewith. In other embodiments supporting surface 37 may support a base provided without any notches. Each of the terminal edges 53 is shown to be aligned with a corresponding arm 69a, b or c of fixation sticker 65, extending across the width of the arm. Guidable edge 54 has a distinctive shape so as to be positionable close to a prominent anatomical feature (e.g., the sternal notch for a sternal application, a tibial tuberosity for a tibial application, or any other easy-to-find anatomical landmark). Guidable edge 54 is designed to be located at a predefined distance from the center of base 38, through which IO catheter 92 passes, to assist in properly aligning stabilizer 40 relative to the penetration site. This is because supporting surface 37 and each of the guidable edges 54 is configured with a predetermined geometrical relation, which may be age-specific so as to be appropriate for a human body size of an average age and/or site-specific for a specific anatomical structure, between a guidable edge 54 and the aperture adapted to overlie the penetration site.

Each of the guidable edges 54 is shown to be concave, making them suitable to be positioned adjacent to a prominent anatomical feature such as the sternal notch, but the guidable edges may be configured in other ways in alternate embodiments. All of the guidable edges 54 may be uniformly shaped. In alternate embodiments, each guidable edge may be differently shaped, such as with a different radius of curvature, or differently dimensioned, such as dimensioned with a different distance to the center of the base. By having similarly configured guidable edges 54, the health practitioner performing the penetration operation may conveniently reposition the supporting surface 37 and the base 38 protruding therefrom, depending on the current angle of the health practitioner relative to the anatomical feature and on the configuration of the guidable edge 54. By having differently configured guidable edges, the health practitioner performing the penetration operation may easily position the IO device relative to different anatomical sites. For example, one guidable edge 54 may be configured to facilitate repositioning when it is positioned adjacent to the proximal tibia anatomical landmark location and another guidable edge 54 is positioned adjacent to the sternum anatomical landmark location.

The three notches 41a-c provided in base 38 advantageously allow the health practitioner to stand in one of three different directions relative to the patient, for example while standing behind the head or to the side of the patient, in order to initiate a transfusion operation with use of the IO catheter, thereby enhancing the convenience and ease of use.

More importantly, the three notches 41a-c provide increased flexibility in deciding how the flexible tube 55 of the IO catheter 92 should be connected to an infusion-related component. An important consideration is the location of the infusion tube within the congested environment of an ambulance or helicopter, where the available room surrounding the patient is limited and often crowded with paramedics or other emergency care assistants attempting to provide life-saving care. Since infusion bags are often hung above the patient in such a congested environment, the infusion tube often passes in the space above the patient as well. An emergency care assistant is therefore liable to unknowingly collide with the infusion tube and cause the corresponding needle to become dislodged from the patient's body. A stabilizer configured with spaced and differently positioned notches advantageously helps to secure the infusion tube in a position that is most protected and user friendly to the emergency care assistant while the patient is being transported.

Figure 5:
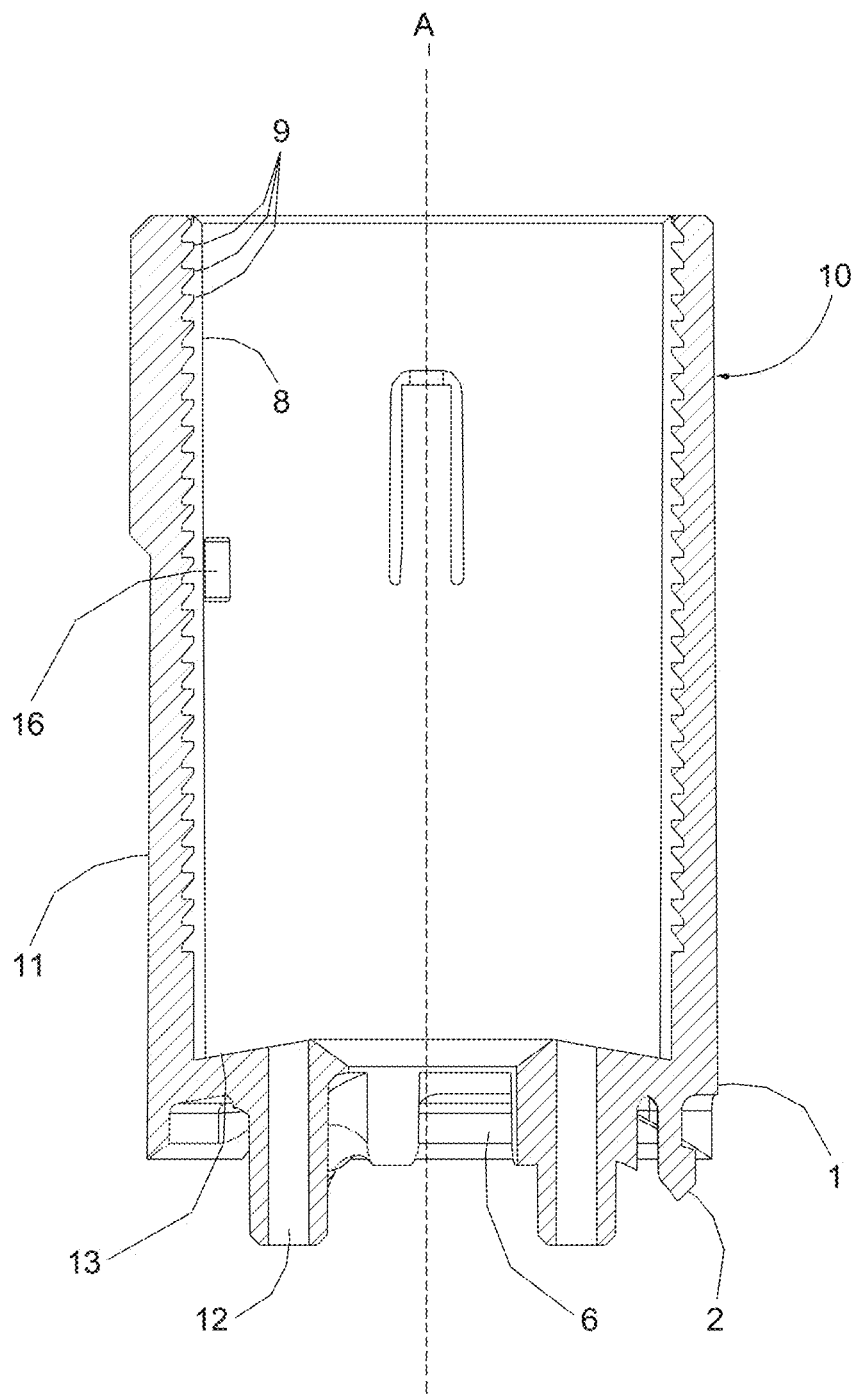
FIG. 5 is a cross-sectional view of an inner tube of the device of FIG. 1.
Figure 5A:
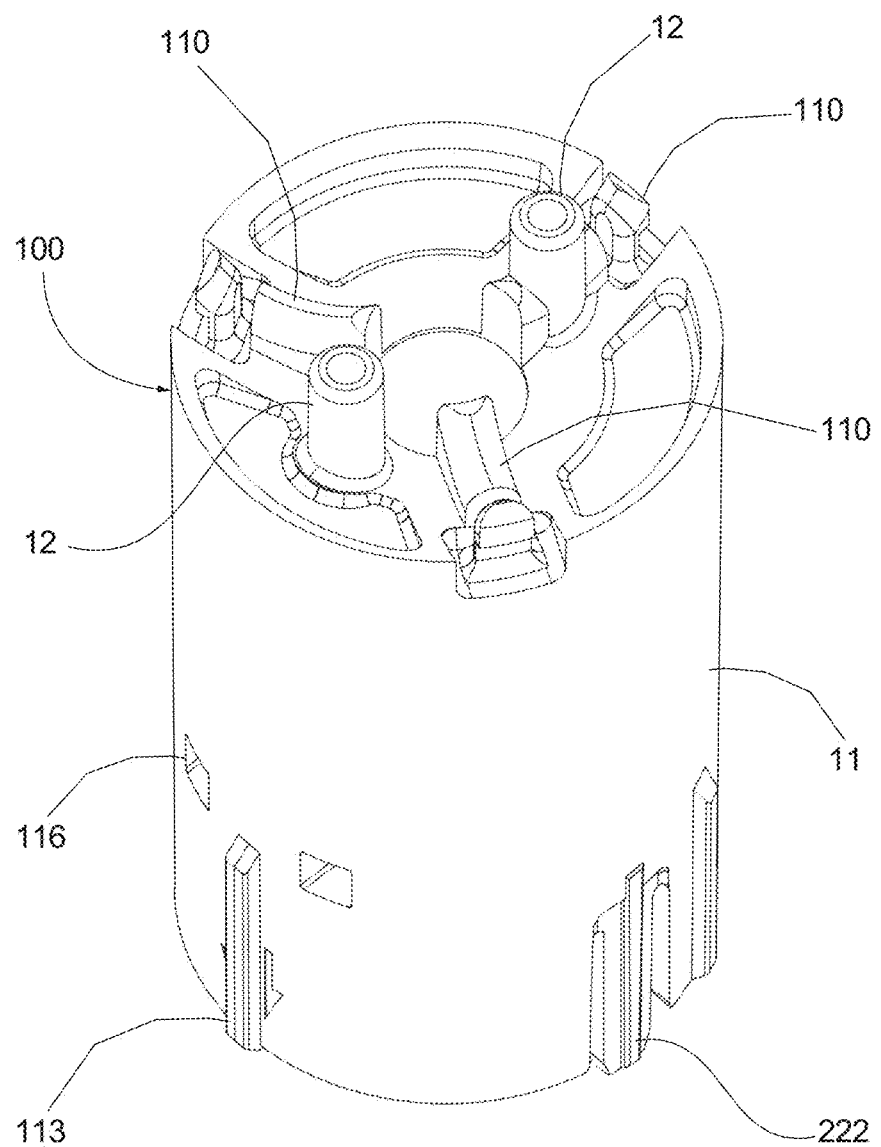
FIG. 5A is a top perspective view of an inner tube of the device of FIG. 1B.

FIG. 5 illustrates a cross sectional view of inner sleeve 10, prior to the outer sleeve member 15 being mounted thereabout. FIG. 5A illustrates the annular distal wall 113 of the inner sleeve 100. Outer circumferential surface 11 of inner sleeve 10, 100 may be formed with an aperture 16, 116 within which safety latch 45 (see FIG. 1) is insertable. Inner surface 8 of inner sleeve 10 is formed with a plurality of axially spaced grooves 9, each of which is recessed from inner surface 8. In one embodiment, the grooves 9 have a triangular cross section. Other shapes/cross sections of the grooves are possible in other embodiments. At the distal end of the inner sleeve, one or more passageways 12 spaced radially outwardly from longitudinal axis A, extend through, and distally protrude from, an annular distal wall 13 of the inner sleeve 10, the purpose of which is to ensure alignment between stabilizer base 38 and the IO device 30 (particularly inner sleeve 10), by the alignment of passageways 12 of inner sleeve 10 to one of each of notches 41a-c in stabilizer base 38. The protrusions 12 are adapted to receive a corresponding probe needle 27 and are aligned with holes 46 in base 40.

The distal end of inner sleeve 100 also includes one or more protrusions 110 spaced radially outwardly from longitudinal axis A, extend through, and distally protrude from, an annular distal wall 113 of the inner sleeve 100. The protrusions 110 are aligned with notches 41a or more (41b, 41c etc.,) provided in base 40.

As shown in FIG. 5A, the protrusion 110 and passageway 12 may be formed monolithically as one part.

Distal wall 13 has a central opening 6 through which the intraosseous needle assembly is received after the outer sleeve member is mounted about the inner sleeve. A plurality of circumferentially spaced J-shaped attachment elements 2 each of which releasably engageable with a corresponding set of constricting elements 32a and 32b (see FIG. 4) protrude distally from the distal edge 1 of outer surface 11.

Figure 6:
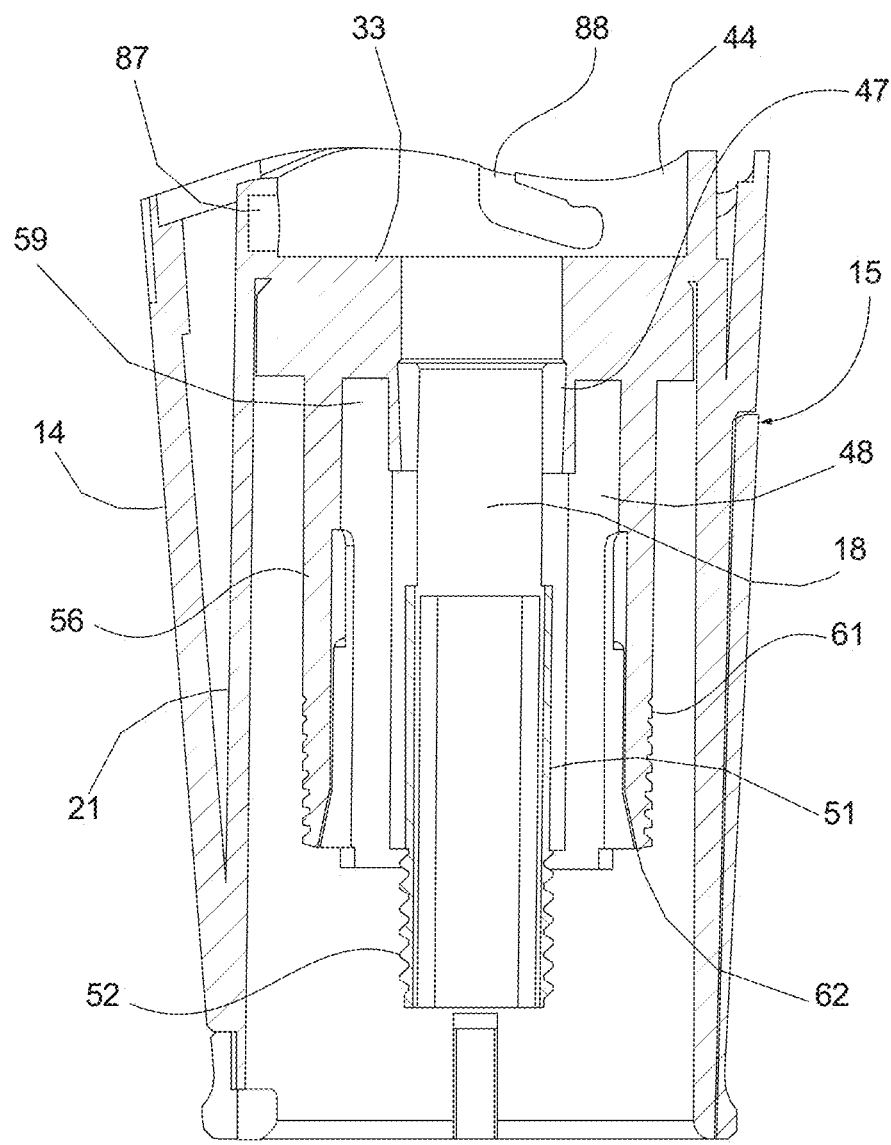
FIG. 6 is a cross-sectional view of an outer sleeve member of the device of FIG. 1.
Figure 6A:
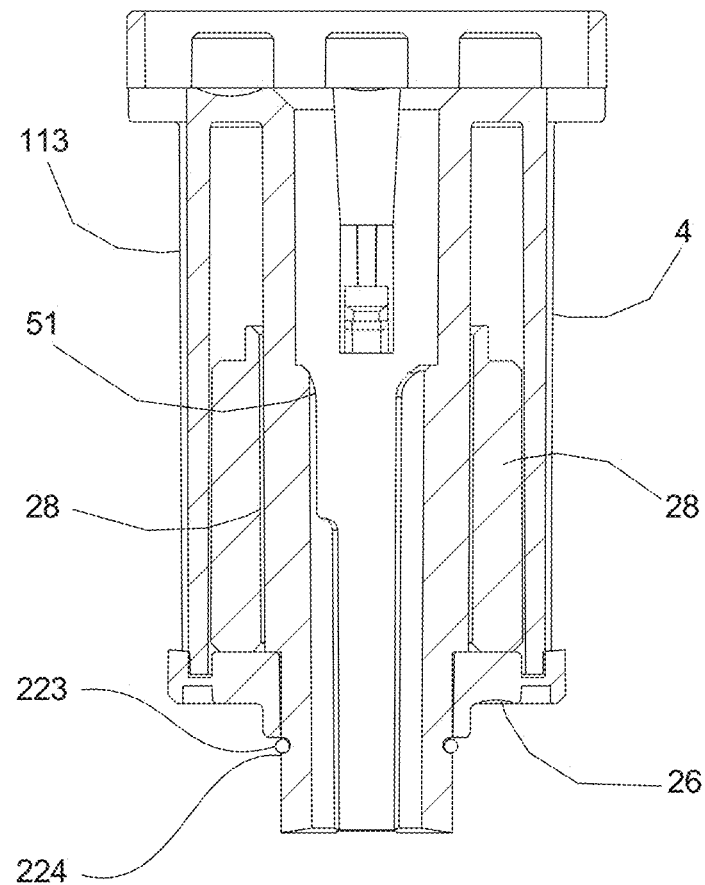
FIG. 6A is a cross-sectional view of an outer sleeve member of the device of FIG. 1B.
Figure 6B:
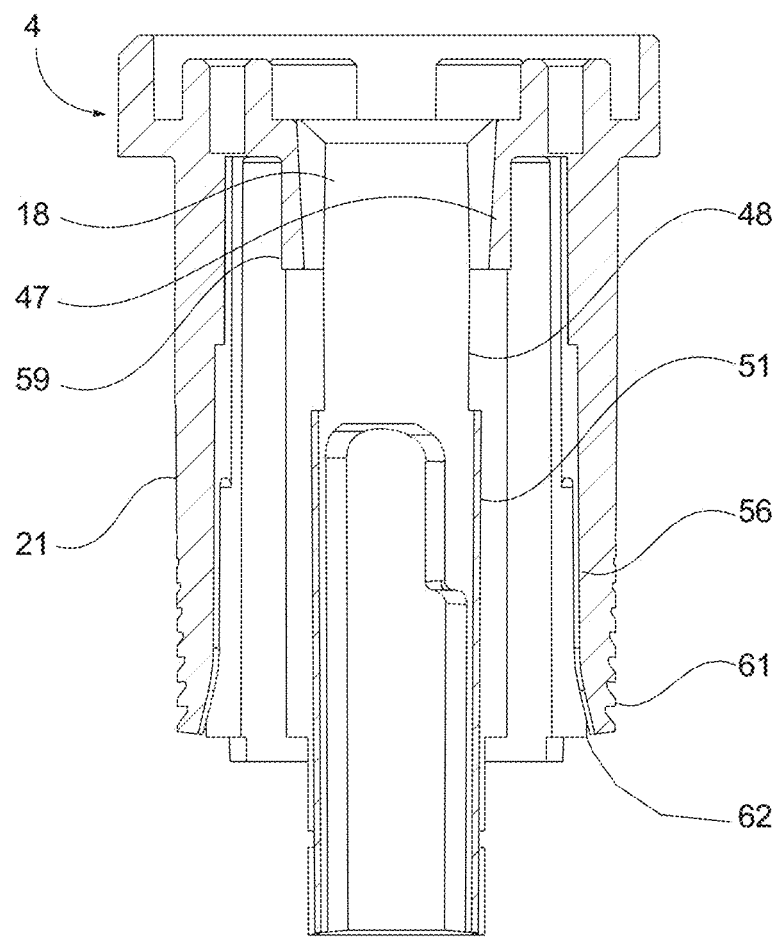
FIG. 6B is another cross-sectional view of the outer sleeve member of the device of FIG. 1B.

FIG. 6 illustrates a cross sectional view of outer sleeve member 15 in one embodiment, showing the inner structure of outer sleeve 20. FIG. 6A illustrates a cross sectional view of body 4 with motion inducer 28 and needle holder 26 (in outer sleeve 200), and FIG. 6B illustrates a cross sectional view of body 4 in a cross section rotated 90 degrees relative to FIG. 6A. Outer surface 21 of the outer sleeve 20 is substantially parallel to the longitudinal axis A of the outer sleeve member 15, which is adapted to be coincident with the longitudinal axis of the inner sleeve. Outer surface 14 of the grip 16 extending from a distal region of outer surface 21 is oblique with respect to longitudinal axis A.

The inner diameter of outer surface 21 is substantially equal to the outer diameter of outer surface 11 of the inner sleeve in the embodiment shown in FIG. 5.

With continued reference to FIG. 6, an annular intermediate surface 33 is formed with central opening 18 and is substantially perpendicular to longitudinal axis A (shown in FIG. 5). A rigid tube 47 having a window (i.e., aperture) 48 extends distally from intermediate surface 33. An annular mounting post 51 is extends from the inner surface of tube 47 distal to window 48. In one embodiment, annular mounting post 51 includes external threading 52 at its distal end which protrudes from tube 47. Two elongated, narrow flexible catches 56 each spaced radially outwardly from tube 47 extend distally from intermediate surface 33. The distal portion of each catch 56 is configured with rounded teeth 61 at the outer edge thereof to facilitate engagement with grooves 9 of inner sleeve 10 (see FIG. 5), and is configured with a curved, or otherwise oblique, inner edge 62 that extends towards outer surface 21. The clearance 59 between tube 47 and catches 56 constitutes a spring chamber within which proximal spring 63 (see FIG. 2) is receivable.

While driving member hub 5 is separated from outer sleeve member 15, Luer-Lock fitting 57 is inserted into the interior of mounting post 51 and engaged with the inner surface of the latter. At the same time, flexible tube 55 connected to Luer-Lock fitting 57 protrudes distally from nut 29. While Luer-Lock fitting 57 is being inserted into the interior of mounting post 51, the outer periphery of Luer-Lock fitting 57 forces decoupling element 77 to be displaced radially outwardly momentarily until returning to be displaced radially inwardly under the influence of flexible arm 78 such that the narrowing tip of hook-shaped decoupling element 77 is positioned in pressed engagement with the lip 68 (FIG. 7) of Luer-Lock fitting 57 as shown. Throat portion 7 of driving member hub 5 is then introduced within central opening 18 of outer sleeve member 15 (FIG. 6), so that rod 42 connected to the throat portion will be received within the interior of, and strengthen, tube 55, until elements of driving member hub 5 are engaged with surfaces 19 and 33 of outer tube member 15.

FIGS. 7 and 8 illustrate an embodiment with IO needle assembly 35 and a portion of probe needle assembly 25 when assembled and located at one of different possible axial relative positions therebetween. Motion inducer 28 of probe needle assembly 25 includes a discontinuous tubular periphery 73 and with two diametrically opposed rectangular extensions 74 that radially protrude outwardly from terminal edges of periphery 73. The distal end of each extension 74 includes a wedge-shaped radial expander 76. A narrow flexible arm 78 is spaced radially inwardly from a corresponding extension 74, to accommodate positioning of a spring within the radial clearance 79. The narrow flexible arm 78 is slightly longer than the extension and includes at its proximal end a hook-shaped, snappable decoupling element 77 facing away from periphery 73. An element 72 interconnects extension 74 and arm 78. Arm 78 is in abutting relation with rigid tube 47, and decoupling element 77 is in abutting and pressed relation with a lip 68 extending slightly radially outwardly from the periphery at the proximal end of Luer-Lock fitting 57.

Rod 42 of IO needle assembly 35 is fully inserted/contained within the lumen of flexible tube 55. The proximal end of the tube being integrally formed with, or connected by, a leak-free connection. In various embodiments, such connections may include a threaded connection, adhesion or overmolding to Luer-Lock fitting 57. Rod 42 extends through the interior of Luer-Lock fitting 57 so that its proximal end is receivable in the axial bore formed in the driving member hub throat portion. The blunt distal end 43 of rod 42 is in contact with the solid distal end of bone portal 60.

Figure 9:
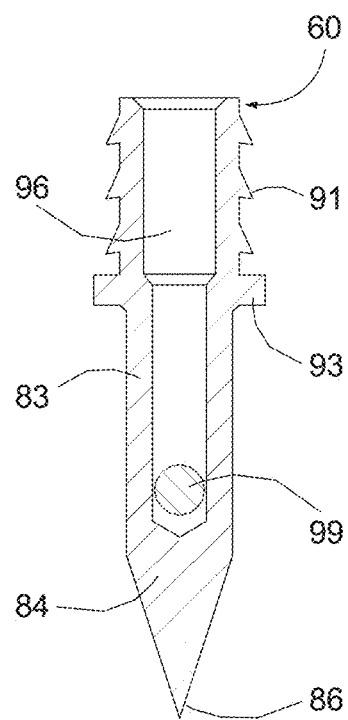
FIG. 9 is a cross-sectional view of a bone portal component of the device of FIGS. 1 and/or 1B.
Figure 9A:
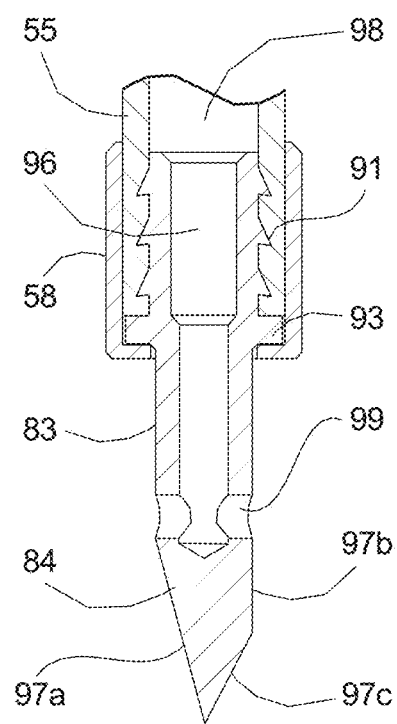
FIG. 9A is another cross-sectional view of a bone portal component of the device of FIGS. 1 and/or 1B.

In the embodiment shown in FIGS. 9 and 9A, bone portal 60 is a sharp stainless-steel member having a varying diameter. A proximal portion 83 of bone portal 60 is hollow and a distal portion 84 thereof is solid and uncompromised. The distal portion 84 of bone portal 60 terminates with a high strength pointed distal end 86 that is suitable to penetrate the bone cortex and to access the bone marrow cavity. Solid distal portion 84 of bone portal 60 may be configured with three sharp-angled facets 97a-c. Bone portal 60 may be connected to flexible tube 55 by a physical connection as will be described below, or may be integral as one unit in an over molding process.

Sharp barbs 91 protrude from the periphery of proximal portion 83 to facilitate radial connection with flexible tube 55. The barbs 91 preferably protrude obliquely and distally from proximal portion 83 to resist detachment from flexible tube 55 during withdrawal of the bone portal 60 from the bone cortex. The inner diameter of flexible tube 55 may be greater than or equal to the outer diameter of barbs 91, allowing the flexible tube 55 to be positioned over the barbs 91 so that the barbs will be able to bite into the wall of the flexible tube when the latter is squeezed, such as by means of crimp ring 58. In various embodiments, crimp ring 58 is formed from a metal material, for example, stainless steel.

A radial abutment 93 extends radially outwardly from the outer wall of proximal portion 83, at a region distal to the barbs 91. Crimp ring 58, when fixed in encircling and pressing relation with respect to the outer surface of flexible tube 55, is secured by an annular distal surface thereof with the distal surface of radial abutment 93. Radial abutment 93 thus fulfills several functions. Firstly, it distally supports and abuts flexible tube 55 both when being attached to barbs 91 and during a transfusion operation. Abutment 93 constitutes an anchoring point for the proximally positioned flexible tube 55, so that forces generated during penetration into the bone cortex will be suitably distributed to pointed distal end 86 to prevent collapse of flexible tube 55. When flexible tube 55 is attached, its outer wall is substantially aligned with the outer edge of abutment 93. Secondly, radial abutment 93 constitutes means by which crimp ring 58 is secured. Thirdly, the abutment is able to contact the outer surface of the bone cortex during a penetration operation, serving as stopping means to prevent overpenetration of the bone portal into the bone when excessive force is applied to the driving member hub.

It will be appreciated that a radial abutment 93 or any other type of shoulder can be provided with other elements of the IO catheter 92, such as the driving rod member 42, the flexible tube 55, and the crimp ring 58.

One or more bores 99 are provided in bone portal 60 in order to facilitate fluid exchange with the bone marrow cavity. Bores 99 are in fluid communication with internal lumen 96 of proximal portion 83 and with internal lumen 98 of flexible tube 55, through which infusion liquids are flowable. In various embodiments, each bore 99 may be elliptically shaped and extend radially outwardly from a lumen 96 at an interface between proximal portion 83 and distal portion 84. The elliptical shape prevents bone chips from entering the bores and lumen 96 during bone penetration. When two bores 99 are employed, they may be positioned diametrically opposite from each other. The liquid flow through the one or more elliptic bores 99 may be equal to the flow that is achievable through a G15 hollow needle or other selected needle gauges.

The stages (or steps) of a penetration operation according to various embodiments will now be described.

Figure 17:
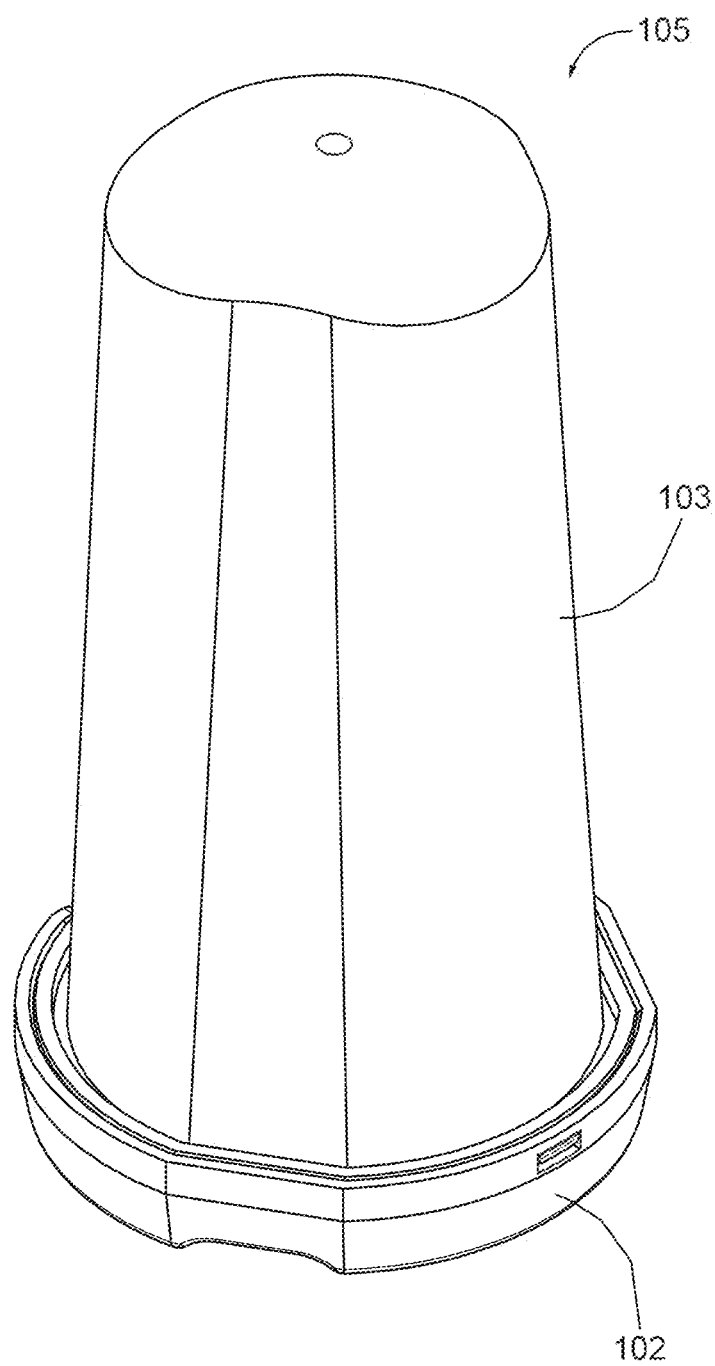
FIG. 17 is a top perspective view of a device package for use with the devices of FIGS. 1 and 1B.

The IO device 30 is removed from the interior of package 105 shown in FIG. 17 after cover 102 is separated from package body 103, and ready for use. This may include removal of safety latch 45 and release liner 66 from the skin-facing side of fixation sticker 65 to expose the adhesive.

FIG. 10 illustrates a pre-penetration cross-sectional view of one embodiment of the IO device 30, along a plane orthogonal to (i.e., angularly separated by 90 degrees from) the plane along which the cross-sectional view of FIG. 1A is taken, showing the IO device 30 positioned adjacent a patient's skin/soft tissue overlying his or her bone.

At the initial stage, the rounded teeth 61 of each catch 56 are spaced proximally from grooves 9 of inner sleeve 10, and the distal end of bone portal 60 is distally spaced from the distal end of probe needles 27 by distance X. Distance X is greater than the average bone cortex thickness and less than the average internal diameter of a marrow cavity, and may be any distance between 1.5 mm and 5 mm, e.g., 3 mm. Each radial expander 76 of motion inducer 28 thereof is in contact with the inner edge 62 (see FIG. 6) of a corresponding catch 56, and each decoupling element 77 protrudes radially inwardly through window 48 of tube 47.

Figure 11:
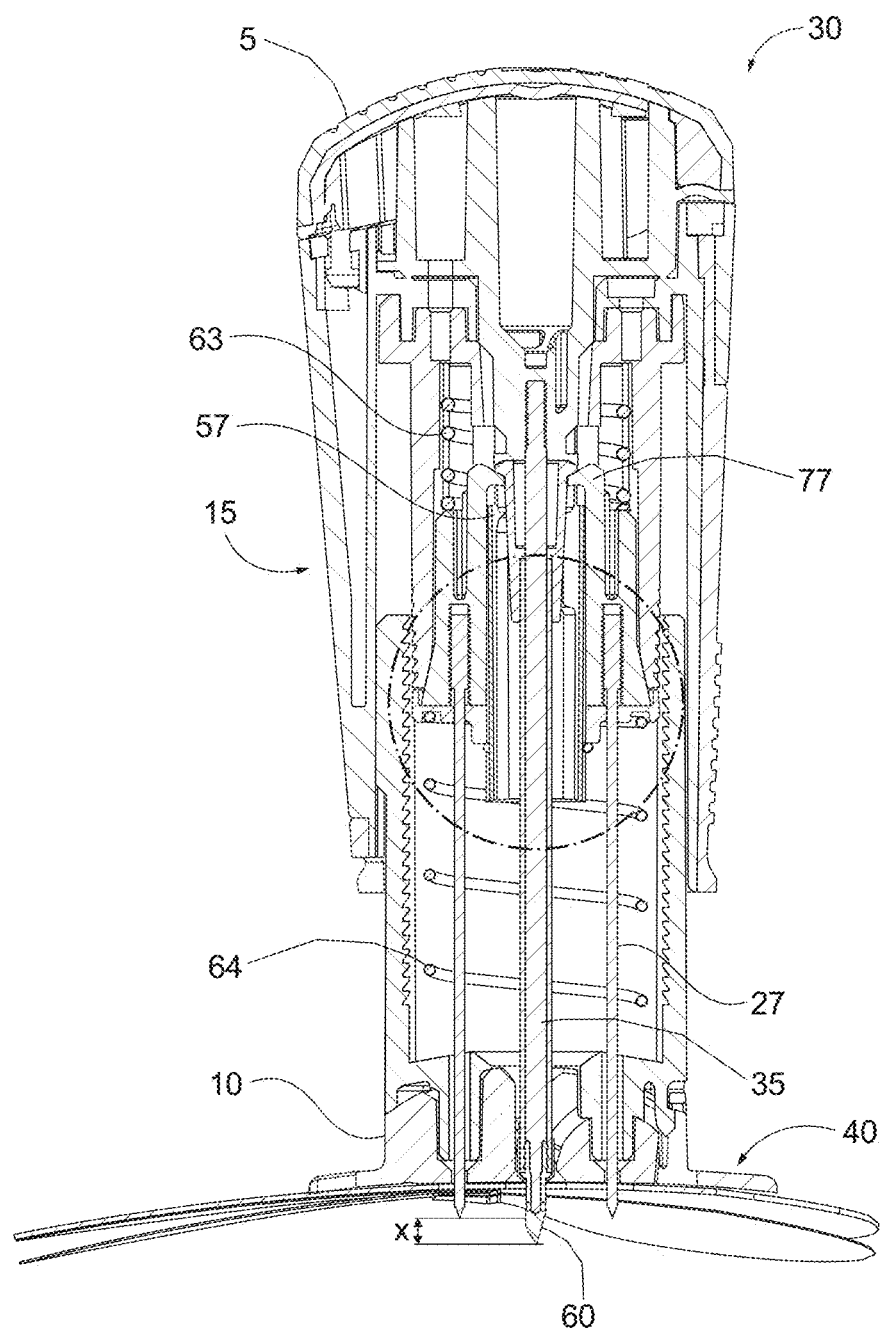
FIG. 11 is a cross-sectional view of the device of FIG. 1 after a driving force has been applied to a driving member hub that causes outer sleeve member to be distally displaced with respect to inner sleeve of the device.
Figure 11A:
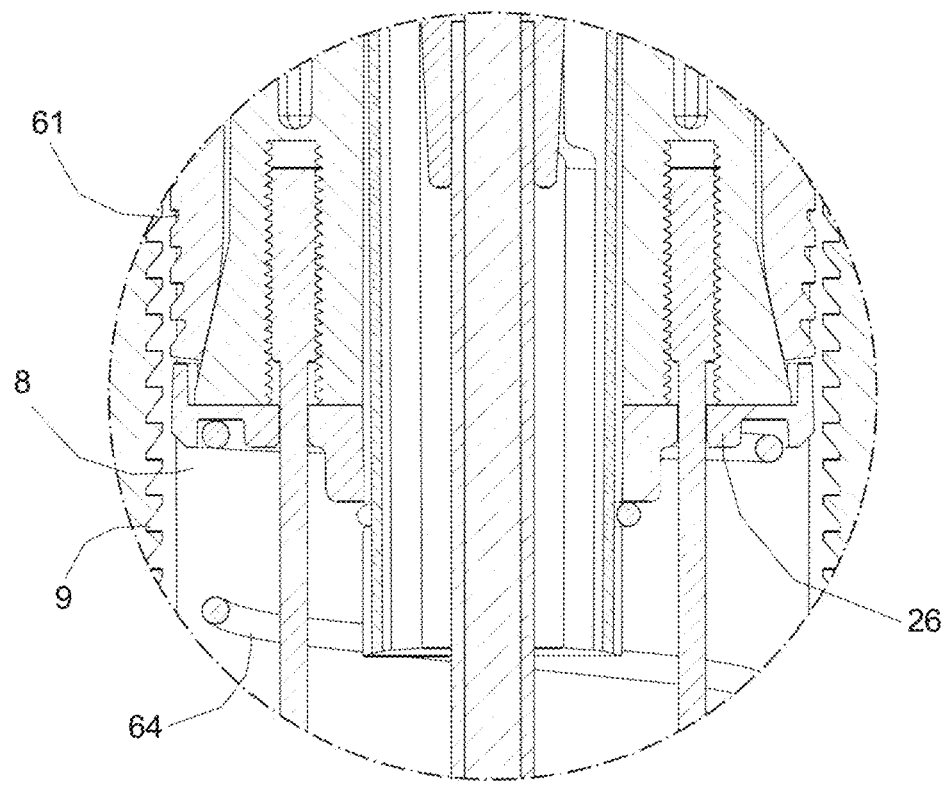
FIG. 11A is a detailed view of FIG. 11.

FIGS. 11 and 11A illustrate IO device 30 after the safety latch 45 has been disengaged and a driving force (i.e., manual pressure from a user) has been applied to driving member hub 5 that causes outer sleeve member 15 to be distally displaced with respect to inner sleeve 10, 100 (i.e., in a collapsing/telescoping motion). The probe needles 27 and IO needle assembly 35 are distally displaced in unison, protruding through stabilizer 40 to be exposed and then penetrate through the patient's soft subcutaneous tissue, and the decoupling elements 77 remain in pressed engagement with the lip of Luer-Lock fitting 57. Due to the distal displacement of outer sleeve member 15 relative to inner sleeve 10, teeth 61 of the catch slide along the inner surface 8 of inner sleeve 10 which is formed with grooves 9.

At the second stage, the driving force/manual pressure for initiating distal displacement of outer sleeve member 15 is transmitted to needle holder 26, and the latter in turn transmits the driving force to distal spring 64, causing it to be compressed. If the thickness of the soft subcutaneous tissue is less than distance X, the bone probe of IO needle assembly 35 is likely to start penetrating the bone cortex. Since the penetration depth limiting mechanism has not yet been activated, outer sleeve member 15 will return to its position at the initial stage upon cessation of the driving force and upon the subsequent expansion of distal spring 64, which proximally propels needle holder 26 and the entire outer sleeve member 15 that is connected to the needle holder.

Figure 12:
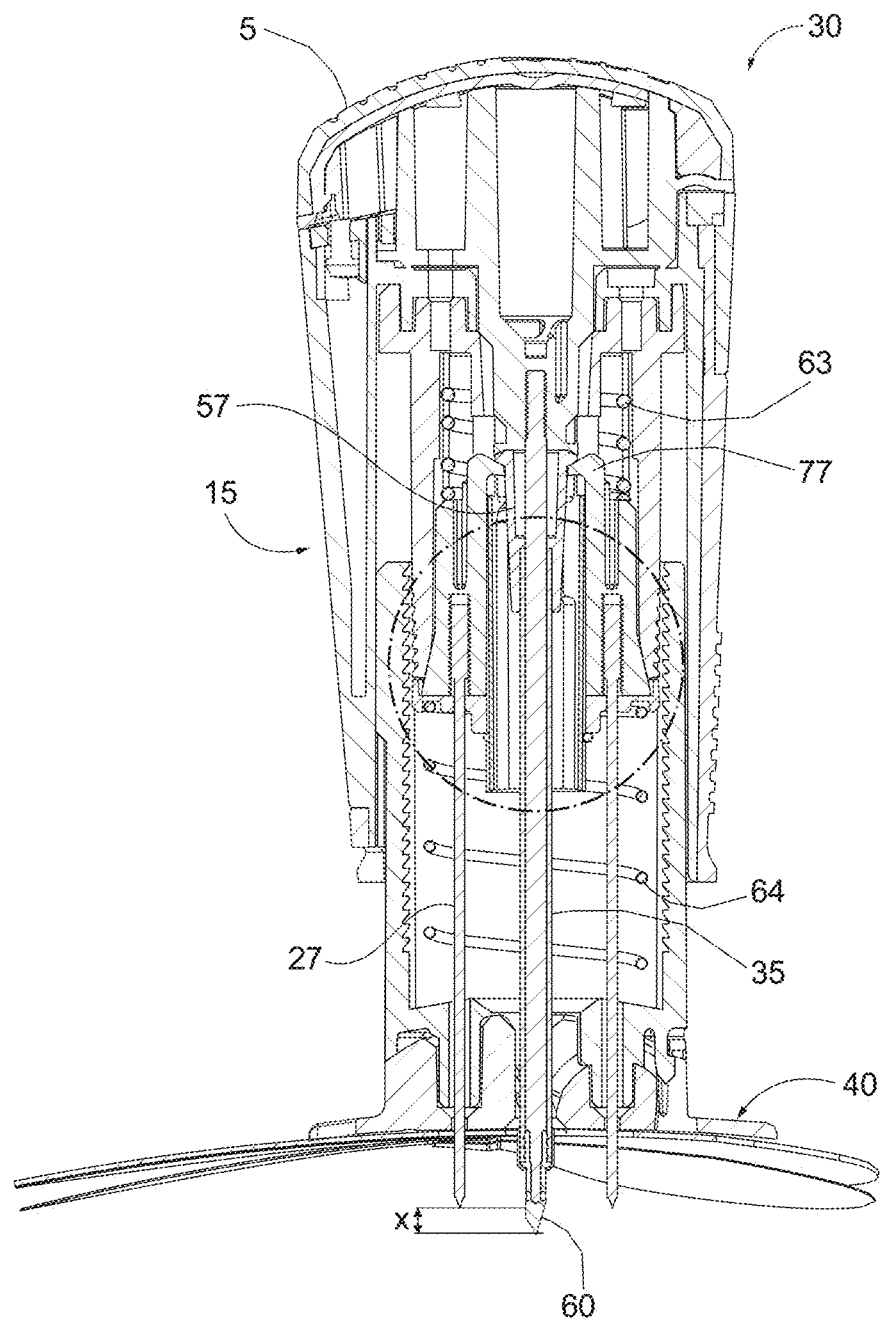
FIG. 12 is a cross-sectional view of the device of FIG. 1 after the outer sleeve member has been additionally displaced distally, until the distal end of probe needles of the device contact a bone cortex.
Figure 12A:
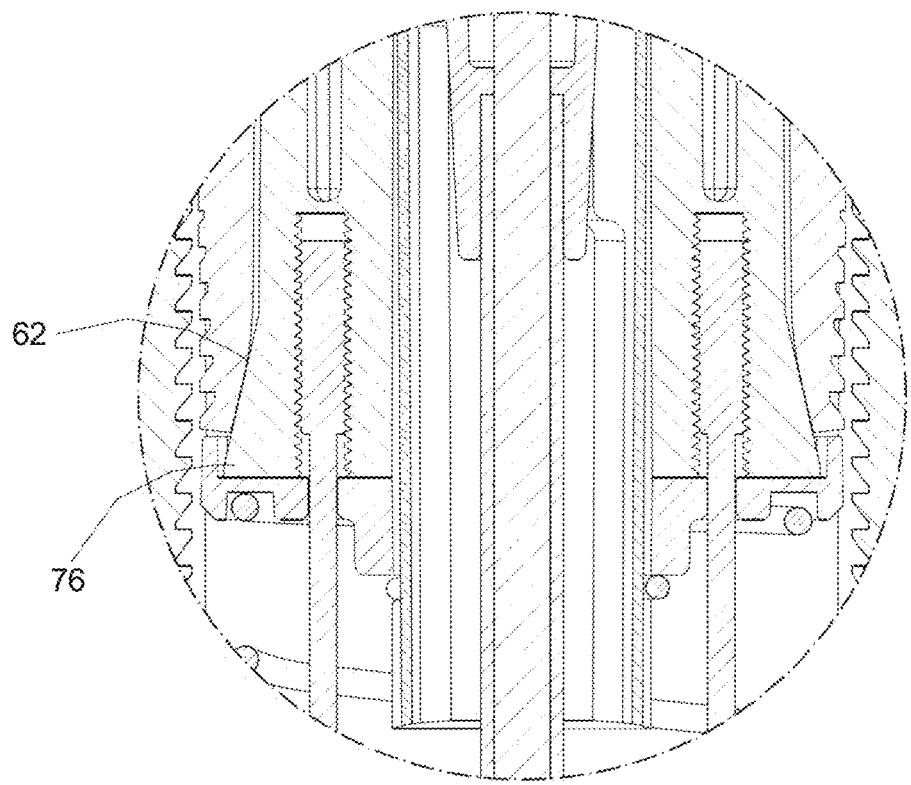
FIG. 12A is a detailed view of FIG. 12.

In the third stage illustrated in FIGS. 12 and 12A, IO device 30 is shown after outer sleeve member 15 has been additionally displaced distally, until the distal end of probe needles 27 contacts the bone cortex. As a result of the reactive force applied by the bone cortex onto the probe needles 27, the latter become immobilized and are therefore prevented from undergoing additional distal displacement. A distal end of each of the probe needles 27 may be configured with a radial protrusion greater than the main probe needle structure, in order to intensify the reactive force applied by the bone cortex onto the radial protrusion of a probe needle.

Disengagement of probe needles 27 from the bone cortex is prevented by means of proximal spring 63, such that the spring force applied thereby (which may be designed to correspond to the bone's reactive force) presses probe needles 27 onto, but not through, the bone cortex. The decoupling elements 77 remain in pressed engagement with the lip of Luer-Lock fitting 57 and the relative position of a radial expander 76 and the corresponding catch inner edge 62 remains unchanged. Although the distal tip of IO needle assembly 35 has penetrated the bone cortex and may have even penetrated the marrow cavity during this third stage and remain separated by the distal end of probe needles 27 by distance X, the distal tip of IO needle assembly 35 is able to be withdrawn upon cessation of the driving force since the penetration depth limiting mechanism has not yet been activated.

Figure 13:
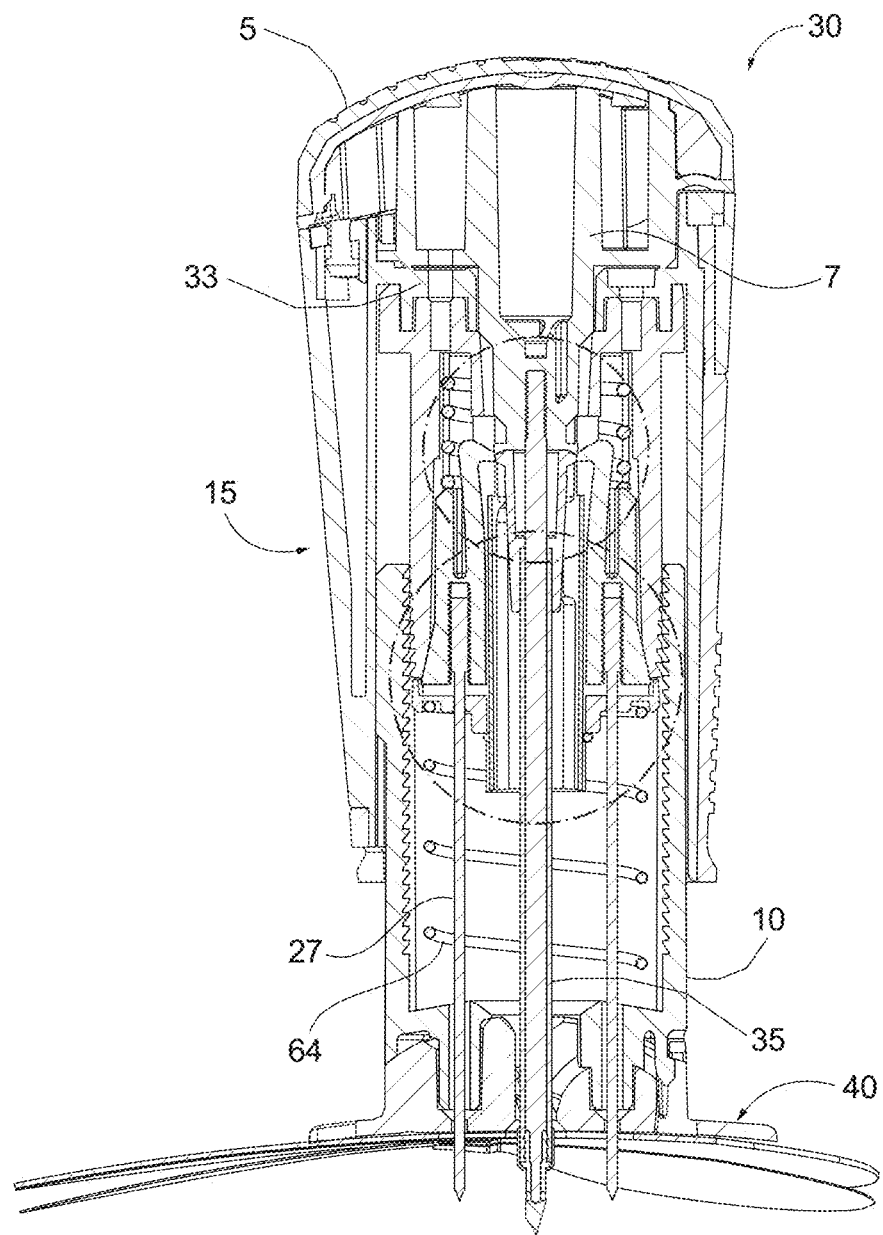
FIG. 13 is a cross-sectional view of the device of FIG. 1 after the manual driving force continues to be applied onto driving member hub and/or outer sleeve member of the device of FIG. 1 following the immobilization of the probe needles.
Figure 13A:
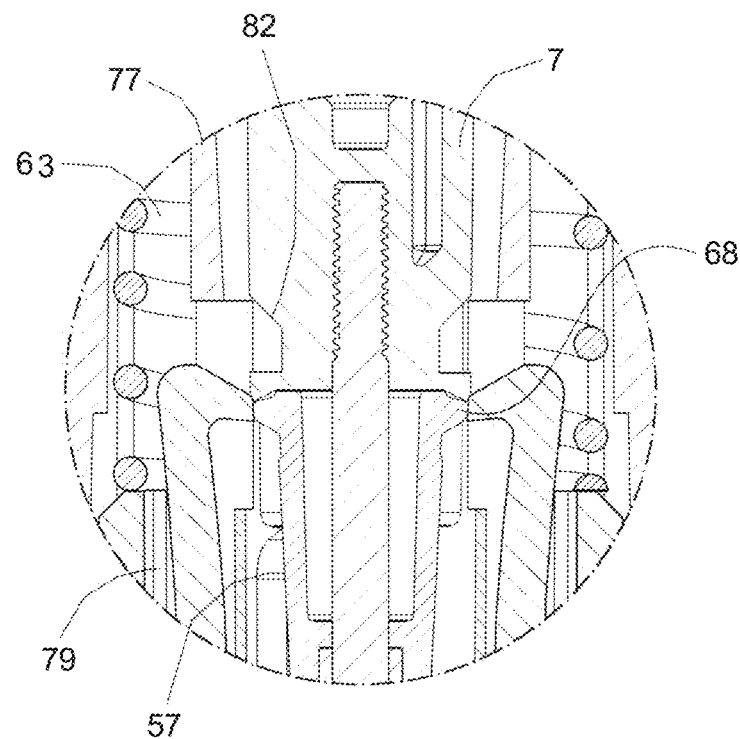
FIG. 13A is a first detailed view of FIG. 13 (top)
Figure 13B:
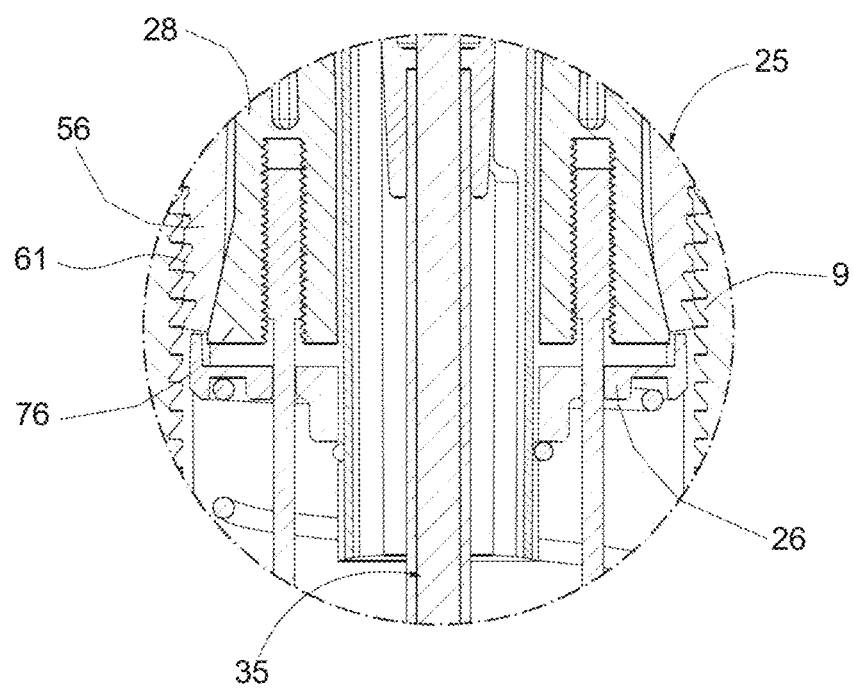
FIG. 13B is a second detailed view of FIG. 13 (bottom)

FIGS. 13 and 13A-B illustrate wherein IO device 30 in the fourth stage, after the manual driving force continues to be applied onto driving member hub 5 and/or outer sleeve member 15 following the immobilization of probe needles 27 during the third stage. The driving force is transmitted through the intermediate surface 33 of outer sleeve member 15 to proximal spring 63, causing it to become compressed upon contact with the immobilized proximal end 79 of each probe needle 27. Proximal spring 63 is biased with a spring force, for example approximately 1.5 kgf, which enables movement of probe needles 27 through the subcutaneous tissue, but proximal spring 63 will compress in response to application of the reactive force by the bone cortex once the probe needles 27 become immobilized.

As a result of the compression of proximal spring 63, driving member hub 5 and IO needle assembly 35 connected thereto are distally displaced relative to probe needle assembly 25. IO needle assembly 35 is consequently caused to penetrate the bone cortex, if it was not already penetrated in one of the previous steps. During the distal displacement of driving member hub 5, throat portion 7 transmits the driving force to lip 68 of Luer-Lock fitting 57. The distally directly force applied by lip 68 onto the narrowing tip of each hook-shaped decoupling element 77 causes the decoupling elements to undergo a jerking motion whereby they are displaced radially outwardly and released from lip 68, and their position and the position of the entire probe needle assembly 25 relative to the distally displaced outer sleeve member 15 is changed. Consequently, decoupling elements 77 are caused to be proximally spaced by a position slightly beyond lip 68 but distal to notch 82, which is radially recessed from the throat portion 7 of driving member hub 5 at a region near the distal edge of the throat portion.

The combination of driving member hub 5, motion inducer 28, Luer-Lock fitting 57, proximal spring 63, and decoupling elements 77 as described above may be considered as a release mechanism.

Figure 14:
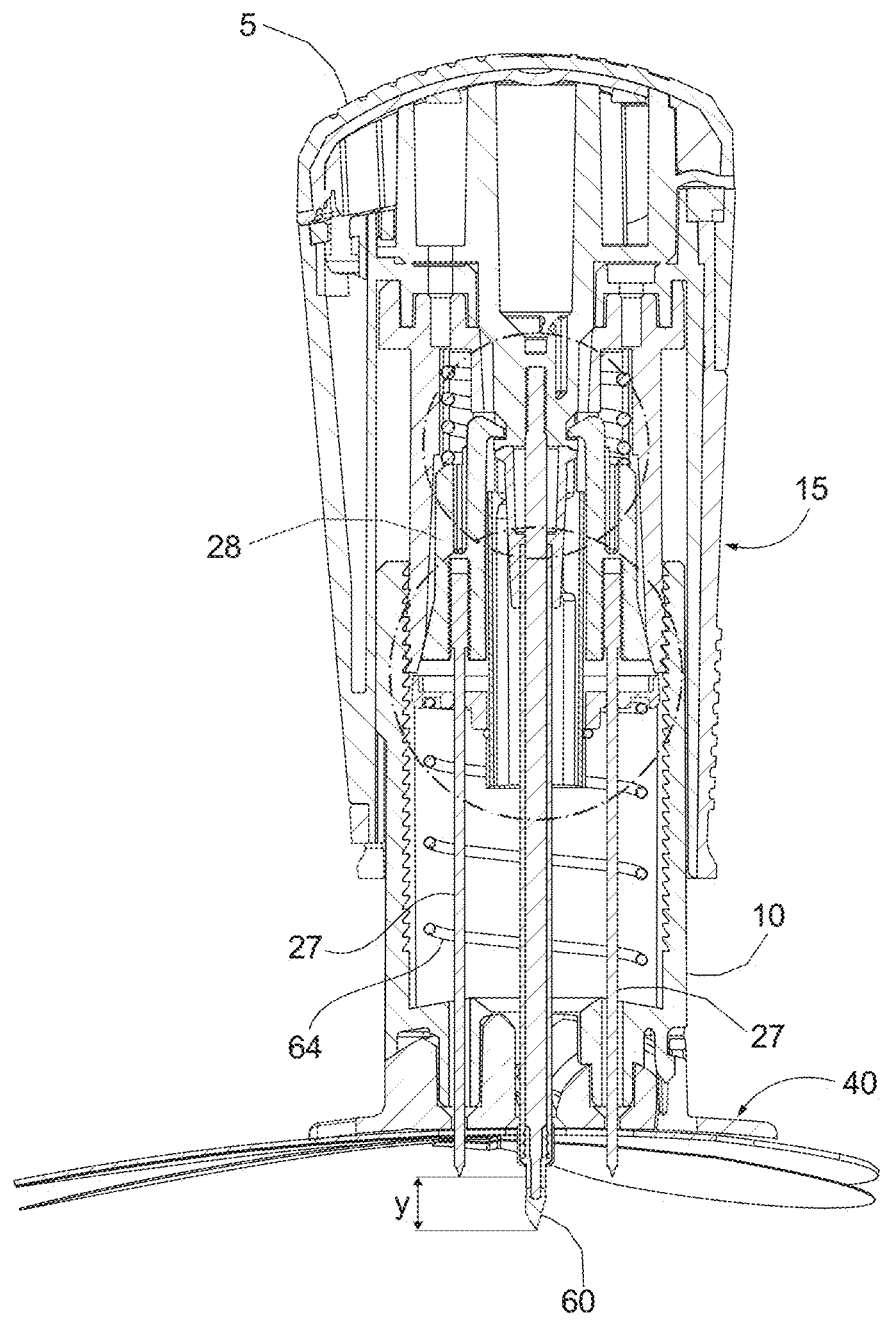
FIG. 14 is a cross-sectional view of the device of FIG. 1 with continued application of the manual driving force.
Figure 14A:
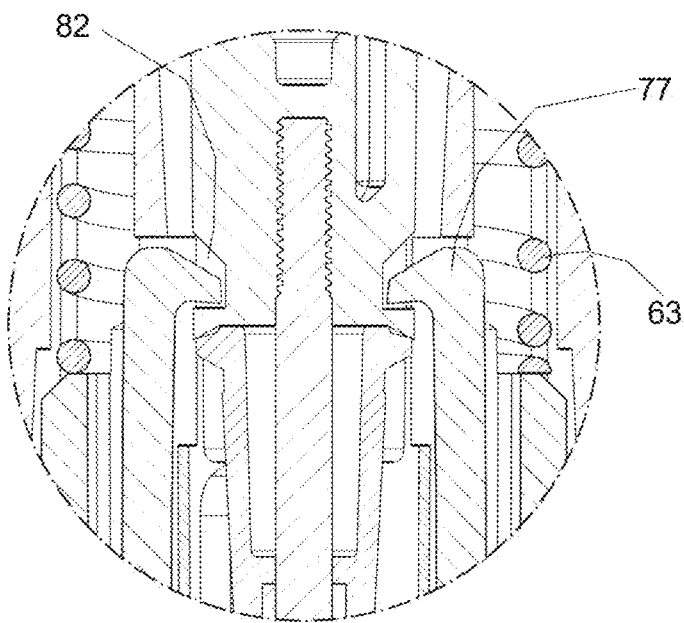
FIG. 14A is a first detailed view of FIG. 14 (top)
Figure 14B:
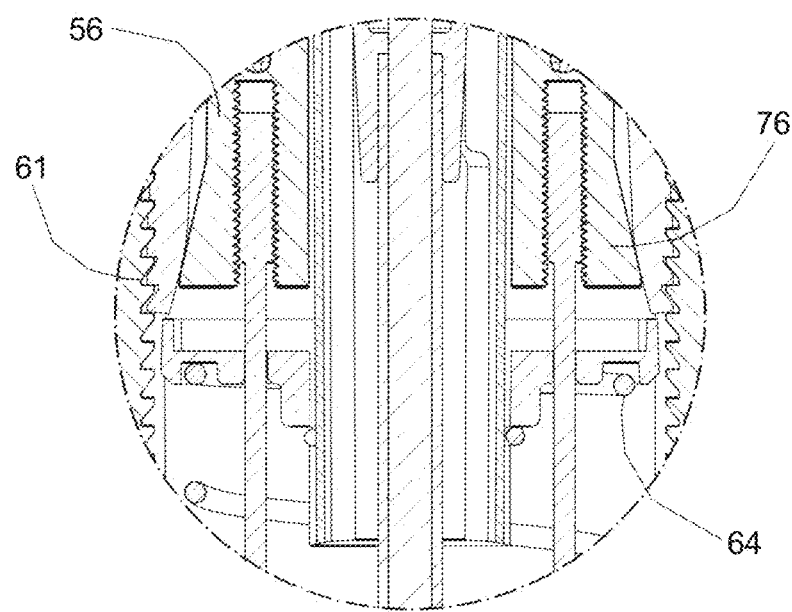
FIG. 14B is a second detailed view of FIG. 14 (bottom)

As the driving force continues to be applied during the fifth stage shown in FIGS. 14 and 14A-B, catch 56 is urged additionally radially outwardly by the radial expander 76 while its teeth 61 are received in the corresponding grooves of inner sleeve 10, causing outer sleeve member 15 to be mechanically locked to inner sleeve 10 and preventing any additional distal displacement of the outer sleeve member. The distal end of IO needle assembly 35 is thus deployed to the predetermined and maximum depth within the bone cortex which is separated from the distal end of probe needles 27 by distance Y which is greater than distance X of FIG. 11, being able to access the bone marrow cavity (see FIG. 15A). Distance Y is the sum of distance X and the incremental axial displacement of the outer sleeve member relative to the inner sleeve during the fourth and fifth stages, e.g., 3 mm.

The combination of driving member hub 5, inner sleeve grooves 9, catch 56, proximal spring 63, and radial expander 76 as described above may be considered as a penetration depth limiting mechanism. At the same time, the distal displacement of outer sleeve member 15 relative to motion inducer 28 causes the decoupling elements 77 to be received within each corresponding notch 82, resulting in an audible and tactile click that is indicative to the user that IO needle assembly 35 has been deployed to the predetermined depth.

In addition to the audible feedback sensed by the user upon achieving penetration to the predetermined depth, the user also advantageously receives terminal feedback. That is, the user is made aware that no further penetration into the bone is possible after the predetermined depth has been achieved by being unable to move outer sleeve member 15. Instead of the feeling sensed during stages 2-5 that outer sleeve member 15 was being distally displaced in response to application of the driving force, the user senses a lack of outer sleeve distal movement, or even a lack of any outer sleeve movement, despite the application of a driving force onto driving member hub 5. This lack of outer sleeve distal movement constitutes terminal feedback that provides a more pronounced and longer-duration feedback than the one-time audible feedback provided by the decoupling element 77 since it provides an indication of penetration to the predetermined depth each time a user attempts to cause additional penetration into the bone cortex.

In one embodiment, following activation of the penetration depth limiting mechanism, inner sleeve 10, 100 and outer sleeve member 15 are non-detachably coupled together. In one embodiment, the distal and proximal movement between inner sleeve and outer sleeve member is prevented so that spring 64 remains compressed and the probe needles 27 are exposed. In another embodiment, proximal movement between inner sleeve 10, 100 and outer sleeve member 15 is possible, as discussed herein. Following actuation of the release mechanism, the outer sleeve member 15 is separated from the IO catheter 92, and therefore the coupled inner sleeve 10, 100 and outer sleeve member 15 constitute a releasable component assembly that also includes the coupled motion inducer 28. Thus, in the sixth stage (see FIG. 15B), the releasable component assembly is pulled and proximally displaced away from the IO catheter 92, so that the transfusion-facilitating components remain penetrated within the bone cortex and in communication with the bone marrow cavity while being accessible to a connector interface that is coupled to a transfusion-facilitating component during a transfusion operation.

Alternatively, the penetration depth-limiting mechanism may be configured such that, when outer sleeve member 15 is mechanically locked to inner sleeve 10, distal movement of the outer sleeve member relative to the inner sleeve 10, 100 is prevented while proximal movement of the outer sleeve member relative to the inner sleeve is made possible, for example, in conjunction with the distal spring 63. Dedicated shaping of the radial expander teeth and of the inner sleeve grooves facilitate the outer sleeve member 15 and the inner sleeve 10, 100 to be non-detachably coupled together in a fashion that is sensitive to the direction of axial displacement. In this embodiment the inner sleeve covers the probe needles 27 and rod 42, to prevent unintentional pricking of the patient and/or health practitioner while detaching the IO device.

FIGS. 15B and 16 illustrates a seventh stage whereby IO catheter 92 remains penetrated within the bone cortex. FIG. 16 illustrates how the flexible tube 55 is plastically reshaped so as to be supported by a curved supporting surface 49 provided in one of the notches 41a-c formed in base 38 of stabilizer 40. This prevents formation of a crease or kink in the flexible tube 55, which may restrict flow of infusion liquids therethrough. The reshaped flexible tube 55 is secured in place by constricting elements 32a and 32b thereon. Although flexible tube 55 is shown to be supported and secured in one of the notches formed in based 38, it will be appreciated that the flexible tube can likewise be supported and secured in any of the other notches, depending on the given position and degree of comfort or convenience of the user.

By fixating Luer-Lock fitting 57 at the proximal end of flexible tube 55 at such a low profile close to base 38 and also adjacent to the skin of the patient, the risk of unintentional withdrawal of IO catheter 92 from the bone due to patient or health practitioner movement is essentially prevented. Also, the three notches 41a-c provided in base 38 advantageously allow the health practitioner to secure IO catheter 92 in one of three different directions depending on other treatment related issues, in order to initiate a penetration or a transfusion operation, thereby enhancing the convenience and ease of use.

At the end of the transfusion insertion operation, the used IO device with the probe needles 27 may be disposed of in the original IO device package 105 shown in FIG. 17, thereby transforming the package into a container for biological waste. Additionally, if needed, the package 105 can serve as a container for biological waste for IO catheter 92 at the end of the transfusion operation.

In embodiments where the proximal movement of the outer sleeve member 15 over the inner sleeve 10, 100 is possible, the safety latch 45 may be coupled again between outer sleeve 20 and inner sleeve 10, 100 at the end of the insertion procedure, thereby preventing unintentional pricking of the patient and/or health practitioner by the probe needles 27. The used IO device 92 may then be safely disposed in a biological waste bin (i.e., a sharps container).

It will be appreciated that the base 38 and stabilizer 40 may be configured in other ways as well insofar as the IO catheter 92 and probe needles 27 are afforded a passageway to subcutaneous tissue and to the adjacent bone cortex. Likewise, the base 38 and stabilizer 40 may be dispensed with when the releasable component assembly is suitably held during a penetration operation.

In another embodiment, a flexible tube is not employed, but rather an inflexible annular IO catheter is used. The IO catheter is connected to or integrally formed with the Luer-Lock fitting and with the bone portal. The driving member, which is connected to the driving member hub and in driving engagement with the Luer-Lock fitting, is inserted into the lumen of the IO catheter, and the penetration operation can be performed as described above.

In another embodiment, a flexible tube and a separate driving member connected to the driving member hub are not employed. In this embodiment, the IO catheter comprises a rigid rod constituting the driving member that is integrally formed with the Luer-Lock fitting and with the bone portal and formed within an axial passageway through which liquid is flowable. The driving member hub is in driving engagement with the Luer-Lock fitting and the penetration operation can be performed as described above.

In other embodiments, the driving member hub is fixedly and detachably connected to outer sleeve member 15 by one of various means such as a Bayonet connector, a threaded connection, and a snap connection. Such a detachable connection will allow the IO catheter to be reassembled onto the driving member, for example, when used for training purposes.

Figure 18:
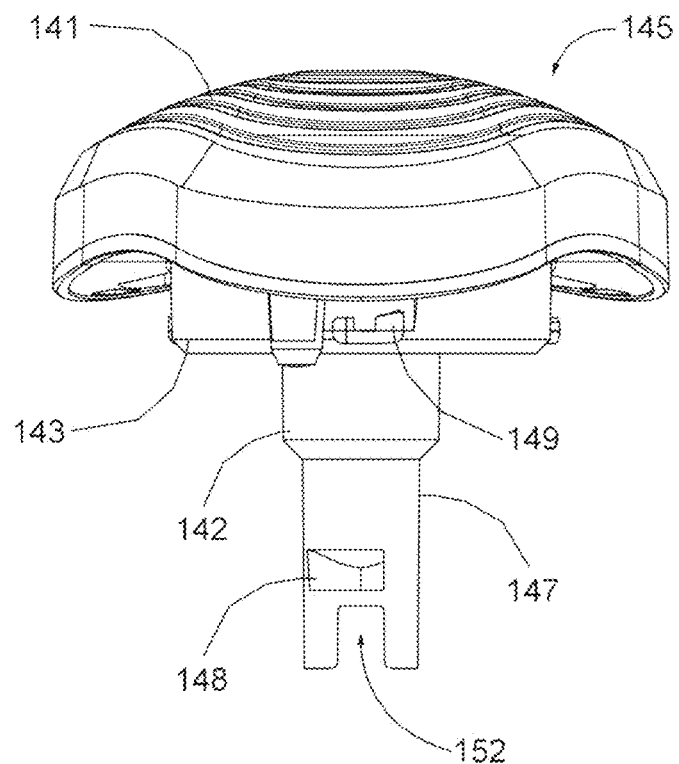
FIG. 18 is a plan view of an embodiment of a driving member hub for use with the devices of FIGS. 1 and 1B.

FIG. 18 illustrates an embodiment of a driving member hub 145 which is configured with a secure and speedy to couple Bayonet-shaped connector. Driving member hub 145 includes a mount 143 for a plurality of outwardly protruding pins 149 of the Bayonet-shaped connector that is fixed to the distal side of a domed proximal surface 141 of the hub. The domed proximal surface 141 may have a raised/embossed/grooved pattern to improve a user's grip on/manual engagement thereof (also see the similar pattern on the surface of hub 5 in FIG. 1). Each pin 149 is configured to be inserted into a corresponding groove formed in the annular wall 44 of outer sleeve member 15 which is proximal to intermediate surface 33 (see FIG. 6). Each of the grooves, for example, grooves 87 and 88, may be differently shaped. After a pin 149 is received in each corresponding groove, driving member hub 145 is rotated in a first rotational direction to lock the pins 149 in place. Pins 149 may be loosened and then detached from the grooves upon rotating driving member hub 145 in a second rotational direction which is opposite to the first rotational direction.

In this embodiment, tube 147 is formed with windows (i.e., apertures) 148 within each corresponding decoupling element and is received during the fifth stage of the penetration operation to produce an audible and tactile click when the IO needle assembly has been penetrated to the predetermined depth in the patient's bone cortex. The tube 147 extends distally from throat portion 142, which is attached to the distal surface of mount 143. Throat portion 142 has a slightly larger diameter than tube 147. The distal end of tube 147 is formed with a notch 152 through which the lip of the Luer fitting radially extends when the distal side of the lip is secured by the decoupling elements during the first, second and third stages of the penetration operation.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims. Although embodiments have been disclosed, the invention is not limited thereby.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other examples are also within the claims.

In general, any combination of disclosed features, components and methods described herein is possible. Steps of a method can be performed in any order that is physically possible.

All cited patents, patent publications and non-patent references are incorporated by reference herein in their entireties.

We claim:

1. A manual intraosseous device for introducing a bone portal to a predetermined depth relative to a surface of a target bone, comprising:
    an intraosseous needle assembly including an intraosseous catheter configured to facilitate transfusion of fluids and aspiration of bone marrow and having a bone portal adapted to penetrate into subcutaneous tissue adjacent the target bone and the cortex of the target bone and a flexible tube configured to convey liquids to and from the bone marrow of the target bone, and a driving member releasably attached to the intraosseous catheter and by which a manual axial force is transmittable to the intraosseous catheter to initiate axial penetration into the subcutaneous tissue and cortex of the target bone;
    an inner tubular sleeve arranged concentric to the intraosseous catheter;
    an outer sleeve member including an outer sleeve arranged concentric to the inner sleeve and being axially displaceable relative to an outer surface of the inner sleeve and the outer sleeve member operably connected to the driving member, and wherein the driving member engages the outer sleeve member;
    a probe needle assembly engaged with the outer sleeve member and at least partially received within an interior of the inner sleeve, and including at least one bone cortex-contacting probe needle;
    a proximal spring positioned within the outer sleeve member, operably connected to the probe needle assembly, and configured to limit the depth that the bone portal penetrates the target bone; and a distal spring positioned within the inner sleeve, operably connected to the probe needle assembly, and configured to move the outer sleeve member to a starting position if the bone portal penetrates the target bone cortex to the predetermined depth, to prevent any additional distal displacement of the bone portal; and
    a stabilizer including a base configured to detachably couple with a distal end of the inner sleeve and having at least one notch sized and shaped to receive at least a portion of the flexible tube therein.

2. The intraosseous device of claim 1, further comprising a body disposed within the outer sleeve and in a concentric relation with inner sleeve.

3. The intraosseous device of claim 2, wherein the body includes an annular mounting post, and further comprising a motion inducer for securing the at least one probe needle, the motion inducer being insertable through the annular mounting post.

4. The intraosseous device of claim 3, wherein the motion inducer includes a discontinuous tubular periphery and two diametrically opposed rectangular extensions that radially protrude outwardly from terminal edges of periphery, the distal end of each extension including a wedge-shaped radial expander.

5. The intraosseous device of claim 1, wherein an inner surface of the outer sleeve includes at least one axial slot formed therein, and wherein the outer surface of inner sleeve includes at least one protrusion protruding radially outwardly therefrom and configured to insertably engage the at least one axial slot, whereby the engagement of the at least one protrusion within the at least one axial slot maintains the inner sleeve and outer sleeve in a concentric relation during axial displacement.

6. The intraosseous device of claim 1, wherein the outer sleeve includes a stopper protruding inwardly from the inner surface of outer sleeve and configured to limit the proximal displacement of outer sleeve relative to inner sleeve.

7. The intraosseous device of claim 1, wherein the distal displacement of the outer sleeve member relative to the motion inducer causes an audible and tactile click that is indicative to the user that the intraosseous needle assembly has been deployed to the predetermined depth.

8. The intraosseous device of claim 1, further comprising a removeable safety latch disposed between the outer sleeve and the inner sleeve and configured to prevent displacement of the driving member due to an unintentional operation of the intraosseous device.

9. The intraosseous device of claim 1, wherein the stabilizer has an aperture sized and shaped to receive at least a portion of the intraosseous needle assembly.

10. The intraosseous device of claim 9, wherein the stabilizer includes a plurality of notches formed in the base and configured to secure the flexible tube therein.

11. The intraosseous device of claim 10, wherein the stabilizer includes a planar supporting surface having a plurality of terminal edges that are spaced from and facing a corresponding notch, and a plurality of guidable peripheral edges extending between two adjacent terminal edges.

12. The intraosseous device of claim 11, wherein the guidable edges are shaped so as to be positionable close to a prominent anatomical feature and are located at a predefined distance from a center of base to assist in properly positioning stabilizer relative to the target bone to be penetrated.

13. A manual intraosseous device for introducing a bone portal to a predetermined depth relative to a surface of a target bone, comprising:
  an intraosseous catheter configured with a driving member and a bone portal that is penetrable into a cortex of the target bone in conjunction with the driving member, the driving member configured to support the intraosseous catheter;
  an inner tubular sleeve;
  an outer tubular sleeve concentric to, and axially displaceable relative to, the inner sleeve; wherein the driving member is connected to the outer sleeve, by which a manual axial force applied to the driving member is transmittable to the intraosseous catheter to initiate corresponding axial penetration into subcutaneous tissue associated with the target bone and into the cortex of the target bone; and
  a penetration depth limiting mechanism to prevent any additional distal displacement of the bone portal when the bone portal is penetrated within the bone cortex; and a stabilizer including a base configured to detachably couple with a distal end of the inner sleeve and defining at least one notch configured to secure the flexible tube therein.

14. The intraosseous device of claim 13, further comprising an outer sleeve member that includes the outer sleeve and a grip engaging an outer surface of outer sleeve, the outer sleeve member operably connected to the driving member.

15. The intraosseous device of claim 14, wherein the driving member further includes a rod, and a driving member hub configured to engage the outer sleeve member and includes a throat portion that is configured to receive a proximal end of the rod therein.

16. The intraosseous device of claim 14, wherein the penetration depth limiting mechanism includes a proximal spring positioned within the outer sleeve member, configured to limit the depth that bone portal penetrates the target bone; and the penetration depth limiting mechanism includes a distal spring positioned within the inner sleeve, operably connected to the probe needle assembly, and configured to move the outer sleeve member to a starting position if the bone portal penetrates the target bone cortex to the predetermined depth, to prevent any additional distal displacement of the bone portal.

17. The intraosseous device of claim 13, wherein the intraosseous catheter is further configured with an internal lumen through which an infusion liquid or a bone marrow aspirate is flowable, and at least one port by which the internal lumen is positionable in fluid communication with a bone marrow cavity of the target bone, and is connectable with a connector interface that induces flow of the infusion liquid or the bone marrow aspirate when the driving member hub is released from the intraosseous catheter.

18. The intraosseous device of claim 13, further comprising a body disposed within the outer sleeve and in a concentric relation with inner sleeve.

19. The intraosseous device of claim 18, wherein the body includes an annular mounting post, and a motion inducer insertable through the annular mounting post.

20. The intraosseous device of claim 13, wherein the stabilizer has an aperture sized and shaped to receive at least a portion of the intraosseous catheter.

* * * * *